United States Patent
Schwartz et al.

(10) Patent No.: US 8,580,516 B2
(45) Date of Patent: Nov. 12, 2013

(54) METHODS AND COMPOSITIONS FOR DIRECT DETECTION OF DNA DAMAGE

(75) Inventors: David A. Schwartz, Encinitas, CA (US); Stephen J. Kron, Oak Park, IL (US)

(73) Assignee: University of Chicago, Chicago, IL (US)

( * ) Notice: Subject to any disclaimer, the term of this patent is extended or adjusted under 35 U.S.C. 154(b) by 0 days.

(21) Appl. No.: 12/555,668

(22) Filed: Sep. 8, 2009

(65) Prior Publication Data
US 2010/0216132 A1 Aug. 26, 2010

Related U.S. Application Data

(60) Provisional application No. 61/094,521, filed on Sep. 5, 2008.

(51) Int. Cl.
*C12Q 1/00* (2006.01)
*C12Q 1/68* (2006.01)
*G01N 33/53* (2006.01)

(52) U.S. Cl.
USPC ............... 435/6.19; 435/4; 435/6.1; 435/7.1

(58) Field of Classification Search
USPC ....................... 435/4, 6.1, 6.19, 7.1
See application file for complete search history.

(56) References Cited

U.S. PATENT DOCUMENTS

| | | | |
|---|---|---|---|
| 4,268,270 A * | 5/1981 | Gabbay et al. | 436/67 |
| 6,309,825 B1 | 10/2001 | Thomas | |
| 2001/0031739 A1 | 10/2001 | Dare | |
| 2003/0077834 A1 * | 4/2003 | Lim et al. | 436/128 |
| 2004/0018526 A1 * | 1/2004 | Hirose et al. | 435/6 |
| 2006/0148124 A1 * | 7/2006 | Wilson | 438/82 |
| 2007/0173508 A1 * | 7/2007 | Hutchinson et al. | 514/250 |

FOREIGN PATENT DOCUMENTS

WO  WO 92/06378  * 4/1992

OTHER PUBLICATIONS

Murata-Kamiya et al. Nucleic Acids Research. 1999. 27(22): 4385-4390.*
Ono. Chem. Pharm. Bull. 1994. 42(11): 2231-2237.*
Bespalov et al., "Recombinant Phabs Reactive with 7,8-Dihydro-8-oxoguanine, a Major Oxidative DNA Lesion," Biochemistry, 1996:35:2067.
Bruskov et al., "Chemiluminescence Enzyme Immunoassay of 8-Oxoguanine in DNA," Biochemistry, 1999:64:803.
Cadet et al., "Oxidative Damage to DNA: Formation, Measurement and Biochemical Features," Mutat. Res., 2003:531:5.
Chakrabarti et al., "Fluorescent Labelling of Closely-Spaced Aldehydes Induced in DNA by Bleomycin-Fe(III)," Int. J. Radiat. Biol., 1999:75:1055.

(Continued)

*Primary Examiner* — Robert T Crow
*Assistant Examiner* — Joseph G Dauner
(74) *Attorney, Agent, or Firm* — Valauskas Corder LLC

(57) ABSTRACT

The present invention is a method for detecting the extent of DNA damage in a subject suspected of having DNA damage wherein the damage results in the formation of aldehyde moieties in DNA comprising, obtaining a DNA sample from the subject, combining the DNA sample with a fluorescent, chromogenic, pro-fluorescent or pro-chromogenic hydrazine compound to from a fluorescent DNA, detecting the presence of the fluorescent DNA by monitoring the fluorescent emission and quantitating the fluorescent emission thereby determining the extent of DNA damage in the subject.

8 Claims, 16 Drawing Sheets

(56) References Cited

OTHER PUBLICATIONS

Chavez et al., "New Role for an Old Probe: Affinity Labelling of Oxylipid Protein Conjugates by N'-Aminooxymethylcarbonylhydrazino D-Biotin," Anal. Chem., 2006:78:6847.

Dizdaroglu et al., "Free Radical-Induced Damage to DNA: Mechanisms and Measurement," Free Radic. Biol. Med., 2002:32:1102.

Hirose et al,, "Direct Visualization of Abasic Sites on a Single DNA Molecule Using Fluorescence Microscopy," Photochem. Photobiol., 2002:76:123.

Ide et al., "Synthesis and Damage Specificity of a Novel Probe for the Detection of Abasic Sites in DNA," Biochemistry, 1993:32:8276.

Kim et al., "Near Field Optical imaging of Abasic Sites on a Single DNA Molecule," FEBS Lett., 2003:555:611.

Kow and Dare, "Detection of Abasic Sites and Oxidative DNA Base Damage Using an ELISA-Like Assay," Methods, 2000:22:164.

Kubo et al., "A Novel, Sensitive, and Specific Assay for Abasic Sites, the Most Commonly Produced DNA Lesion," Biochemistry, 1992:31:3703.

Kurisu et al., "Quantitation of DNA Damage by an Aldehyde Reactive Probe (ARP)," Nucleic Acid Res., 2001 Suppl. 45.

Makrigiorgos et al., "Fluorescent Labelling of Abasic Sites: A Novel Methodology to detect Closely-Spaced Damage Sites in DNA," Int. J. Radiat. Biol., 1998:74:99.

Park et al., "Assay of Excised Oxidative DNA Lesions: Isolation of 8-Oxoguanine and its Nucleoside Derivatives from Biological Fluids with a Monoclonal Antibody Column," PNAS, 1992:89:3375.

Persinger et al., "Imaging Techniques Used for the Detection of 8-Oxoguanine Adducts and DNA Repair Proteins in Cells and Tissues," Exp. Gerontol., 2001:36:1483.

Soultanakis et al., "Fluorescence Detection of 8-oxoguanine in Nuclear and Mitochondria! DNA of Cultured Cells Using a Recombinant Fab and Confocal Scanning Laser Microscopy," Free Radic. Biol. Med., 2000:28:987.

Struthers et al., "Direct Detection of 8-Oxodeoxyguanine and 8-Oxoguanine by Avidin and its Analogues," Anal. Biochem., 1998:255:20.

Sato, Kousuke, et al., Highly Fluorescent 5-(5,6-Dimethoxybenzothiazol-2-y1)-2'-Deoxyuridine 5'-Triphosphate as an Efficient Substrate for DNA Polymerases, ChemBioChem, Oct. 17, 2011, vol. 12, iss. 15, pp. 2341-2346, Wiley-VCH Verlag GMBH & Co., Weinheim, Germany, DOI: 10.1002/cbic.201100452 (first published online Sep. 2, 2011).

Li, Zhu, et al. Chromo-fluorogenic detection of aldehydes with a rhodamine based sensor featuring an intramolecular deoxylactam, Org. Biomol. Chem., The Royal Society of Chemistry, DOI: 10.1039/c1ob06448g (first published online Sep. 14, 2011).

Jun, Mi Eun, et al., "Turn-on" fluorescent sensing with "reactive" probes, Chem. Commun., Jun. 28, 2011, vol. 47, iss. 27, pp. 7583-7601, DOI: 10.1039/c1cc00014d (first published online May 6, 2011).

Hirose, Wataru et al., Selective Detection of 5-Formyl-2'-deoxyuridine, an Oxidative Lesion of Thymidine, in DNA by a Fluorogenic Reagent, Agew. Chem., Nov. 2, 2010, vol. 122, iss. 45, pp. 8570-8572, Wiley-VCH Verlag GMBH & Co., Weinheim, Germany, DOI: 10.1002/ange.201004087 (first published online Sep. 22, 2010).

Raindlova, Veronika, et al. Direct Polymerase Synthesis of Reactive Aldehyde-Functionalized DNA and Its Conjugation and Staining with Hydrazines, Agew. Chem., Feb. 1, 2010, vol. 49, iss. 6, pp. 1064-1066, Wiley-VCH Verlag GMBH & Co., Weinheim, Germany, DOI: 10.1002/anie.200905556 (first published online Dec. 29, 2009).

Boturyn, Didier, et al., Synthesis of Fluorescent Probes for the Detection of Abasic Sites in DNA, Tetrahedron, Apr. 14, 1997, vol. 53, iss. 15, pp. 5485-5492, Elsevier Ltd., DOI: 10.1016/S0040-4020(97)00235-4 (first published online Mar. 25, 1998).

International Search Report dated Jan. 13, 2010 corresponding to copending PCT/US2009/56262.

Written Opinion dated Jan. 13, 2010 corresponding to copending PCT/US2009/56262.

International Preliminary Report on Patentability dated Mar. 8, 2011 corresponding to copending PCT/US2009/56262.

Anderson et al.; "Human Neutrophils Employ the Myeloperoxidase-Hydrogen Peroxide-Chloride System to Convert Hydroxy-amino Acids into Glycolaldehyde, 2-Hydroxypropanal and Acrolein", J. Clin. Invest. vol. 99, No. 3, Feb. 1997, pp. 424-432.

Hazen et al.; "Human Neutrophils Employ the Myeloperoxidase-Hydrogen Peroxide-Chloride System to Oxidize a-Amino Acids to a Family of Reactive Aldehydes", J. Biol. Chem., vol. 273, No. 9, Feb. 27, 1998, pp. 4997-5005.

Hong et al.; "Formation and genotoxicity of a guanine-cytosine Intrastrand cross-link lesion in vivo", Nucleic Acids Research, Oct. 16, 2007, vol. 35, No. 21, pp. 7118-7127.

Hong et al. "Identification and Quantification of a Guanine-thymine Intrastrand Crosslink Lesion Induced by $Cu(II)/H_2O_2$/Ascorbate". Chem Res Toxicol., May 2006: 19(5); pp. 614-621.

Biotrin OxyDNA Test: Fluorescent Protein Binding Method for the Detection of Oxidative DNA Damage. Instructions for Use, Biotrin International, Catalogue No. B1081DNA, Dec. 2007.

* cited by examiner

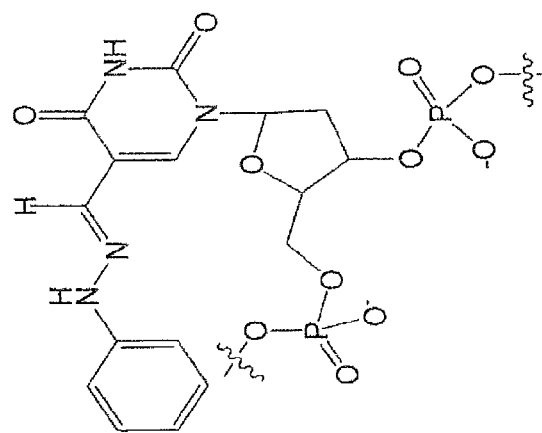
FIG. 4
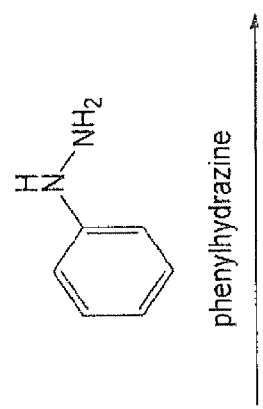
phenylhydrazine
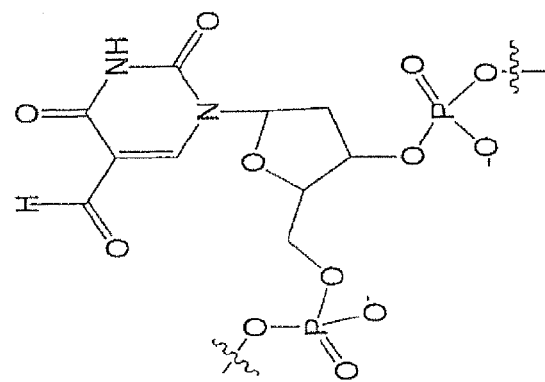

FIG. 8

| | | | |
|---|---|---|---|
| SEQ ID NO: 1 | A | 5'-GTACCTGATGTAGCAGACAGTCTC | 0 mods |
| SEQ ID NO: 2 | B | 5'-GUACCTGATGTAGCAGACAGTCTC | 1 end mod |
| SEQ ID NO: 3 | C | 5'-GTACCTGATGUAGCAGACAGTCTC | 1 center mod |
| SEQ ID NO: 4 | D | 5'-GTACCUGATGUAGCAGACAGTCTC | 2 mods 5b apart (out of ph.) |
| SEQ ID NO: 5 | E | 5'-GTACCTGATGUAGCAGACAGUCTC | 2 mods 10b apart (in phase) |
| SEQ ID NO: 6 | F | 5'-GUACCTGATGUAGCAGACAGTCUC | 2 mods 21b apart (in phase) |
| SEQ ID NO: 7 | G | 5'-GUACCTGATGUAGCAGACAGTCUC | 3 mods uniformly distributed |
| SEQ ID NO: 8 | H | 5'-GTACCUGAUGUAGCAGACAGTCTC | 3 mods closely clumped |
| SEQ ID NO: 9 | I | 5'-GTACCUGAUGUAGCAGACAGTCTC | 3 deoxyuridine control |

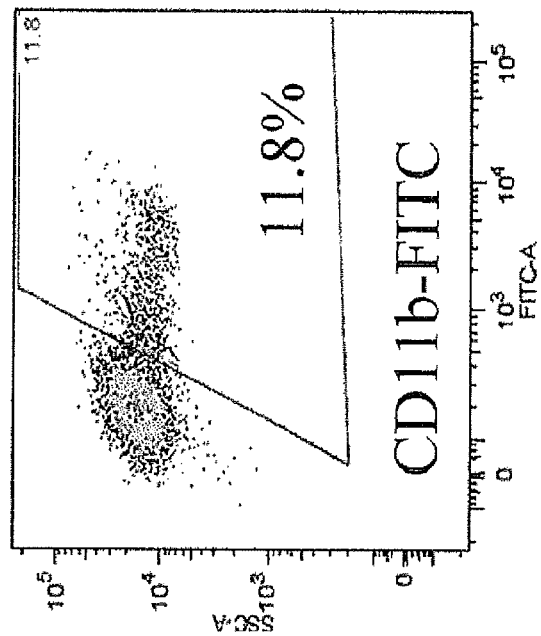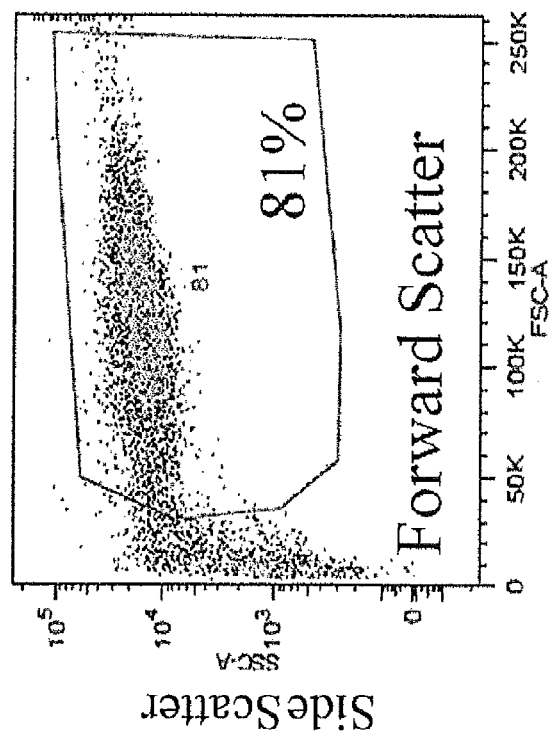
FIG.11A

FIG.11B
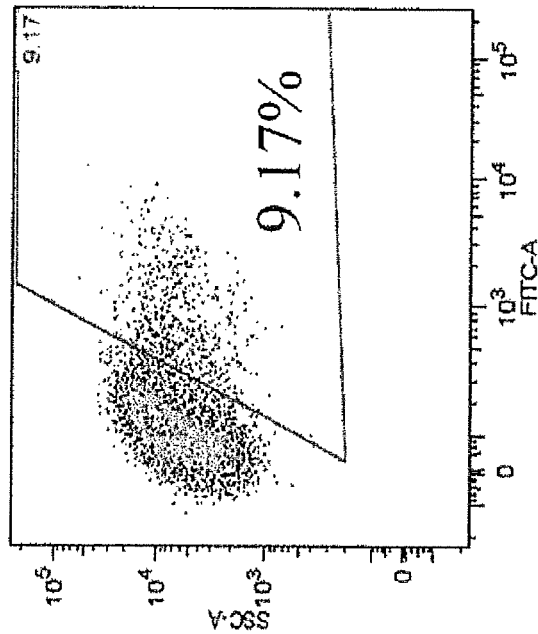
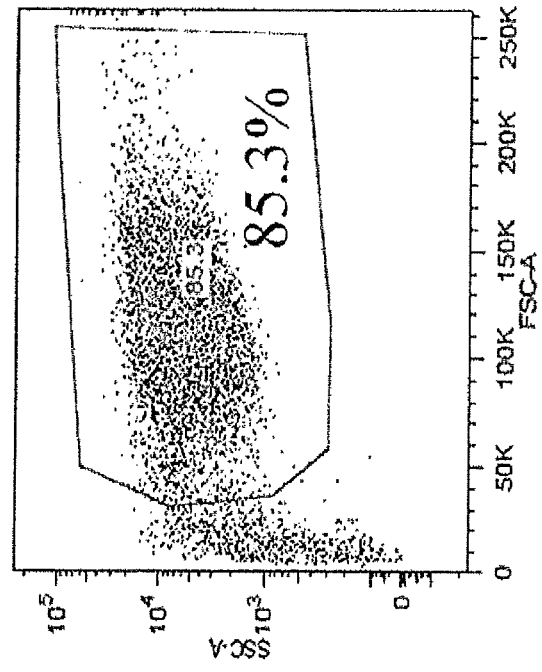

FIG.11C
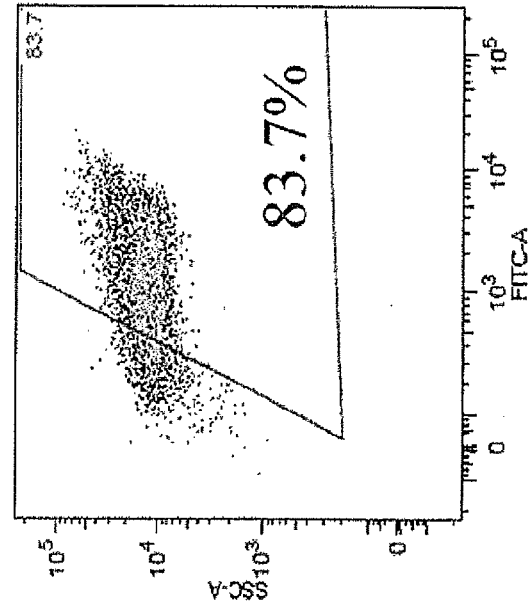
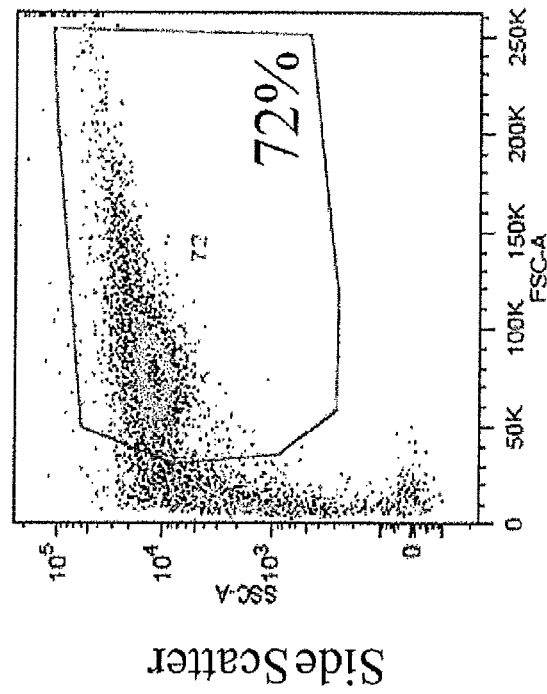

METHODS AND COMPOSITIONS FOR DIRECT DETECTION OF DNA DAMAGE

CROSS REFERENCE TO RELATED APPLICATIONS

This application claims priority to U.S. Provisional Application Ser. No. 61/094,521, filed Sep. 5, 2008, which is incorporated herein in its entirety.

TECHNICAL FILED

The present invention relates to compounds and methods used to label biomolecules for detection and diagnosis. In particular, it relates to fluorescent and pro-fluorescent, chromogenic and pro-chromogenic, hydrazine compounds that when bound to deoxyribonucleic acid ("DNA"), detect damage caused by ionizing radiation, oxidizing chemicals and cellular defects.

BACKGROUND OF THE INVENTION

Oxygen free radicals mediate most ionizing radiation ("IR") damage by attacking DNA bases and the sugar-phosphate backbone. This damage may result as adducts, other covalent modifications and strand breaks that scale directly with IR dose and intensity. Reactive oxygen species (ROS) induce at least twenty common adducts to purines and pyrimidines with 8-oxoguanine (8-oxodG) and 5-formyldeoxyuridine (5-FodU) (FIG. 1) among the most prominent products. Altered base pairing by 8-oxodG, 5-FodU and other lesions can induce mutations and promote cancers including those of breast, prostate, bone marrow, brain, lung, skin, colon, kidney, bladder, and others. One Gray unit "Gy" of absorbed radiation induces many thousands of base lesions along with double strand breaks in each cell, suggesting that dosimetry by direct measurement of base damage might be practical were a rapid, robust and accurate assay available. A promising approach is direct chemical detection of oxidative lesions. The reactivity of the aldehyde moiety of 5-FodU makes it a particularly attractive target because it is the only aromatic aldehyde to be identified in vivo and therefore is ideal as a biomarker.

Extensive literature is available examining the strengths and limitations of different methods of detecting oxidative DNA damage, as reviewed in Cadet et al., Mutat. Res. 531:5 2003; Dizdaroglu et al., Free Radic. Biol. Med. 32:1102, 2002. For this approach to be used in the development of a rapid field capable biodosimetry test, challenges include sufficient sensitivity, specificity, speed and reproducibility to reliably detect as few as 1 lesion in 105 bases from a readily available source of cells. In turn, the lability of some lesions as well as the potential for oxidative damage during work-up for the assay provides additional challenges. Given the wide range of different chemical species described, comprehensive analysis requires complete chemical digestion of purified DNA and analysis by mass spectrometry. For analysis of the adduct 8-oxoguanine (also 8-hydroxyguanine), it is common to use high pressure liquid chromatography ("HPLC")-electrochemical detection or GC-MS to obtain quantitative results. Notably, the two methods can yield very different results from the same samples, which have been ascribed to the chemical derivitization required for the latter method. In turn, the requirement for purification of DNA, complete hydrolysis and complex analytic instrumentation suggest that these methods are not amenable to clinical use, let alone rapid dosimetry of mass casualties. Indirect methods include detection of glycosylase-sensitive sites by alkaline elution or comet assay. Both are compatible with analysis of cells rather than purified DNA, but neither offer sufficient sensitivity nor quantitation. Recent approaches such as detection anti-8-oxoguanine monoclonals (Bruskov et al., Biochemistery 64:803, 1999; Park et al., PNAS 89:3375, 1992), Fabs (Bespalov et al., Biochemistry 35:2067, 1996; Soultanakis et al., Free Radic. Biol. Med. 28:987, 2000) or binding of avidin (Struthers et al., Anal. Biochem. 255:20, 1998) similarly do not require DNA purification and are amenable to detection in cells and tissues (Persinger et al., Exp. Gerontol. 36:1483, 2001), but are subject to a range of artifacts and are relatively less sensitive to clustered damage. Commercial kits for 8-oxoguanine based on antibody, or avidin, detection by enzyme-linked immunosorbent assay ("ELISA"), imaging (Biotrin OxyDNA, Biotrin, Dublin, Ireland) and flow cytometry (HemoGenix OxyFLOW HemoGenix, Colorado Springs, Colo.) are available. However, these formats utilized with these assays, do not yield results over 2 Gy with accuracy and precision having a statistical certainty for rapid triage nor satisfactory for high throughput assays that provide accurate and precise results with a stated statistical certainty over the range of 0.5-10 Gy.

An attractive and comprehensive alternative is to use the chemical reactivity of some oxidized bases to detect their presence in purified DNA and/or in permeabilized cells. The Aldehyde Reactive Probe ("ARP", N-(aminooxyacetyl)-N'-(D-biotinoyl) hydrazine (Ide et al., Biochemistry 32:8276, 1993; Kubo et al., Biochemistry 31:3703, 1992)) represents the most comprehensively studied chemical-based method to detect lesions on DNA caused by oxidative stress. ARP detects abasic sites on DNA by forming an oxime between a substituted aminoxy reagent and the aliphatic aldehyde produced on de-purination (FIG. 3). The reaction condenses a biotinylated aminoxy reagent to covalently link the biotin moiety to the oxidized DNA, and is amenable to quantitation (Kurisu et al., Nucleic Acid Res. Suppl. 45, 2001) and ELISA format (Kow and Dare, Methods 22:164, 2000). In addition to abasic sites, ARP also efficiently reacts with 5-FodU in DNA (Ide et al., 1993 supra) and it is possible that a significant fraction of the reactivity for ARP may derive from 5-FodU rather than abasic sites. ARP is commercially available from Dojindo (Rockville, Md.) and Invitrogen/Molecular Probes (San Diego, Calif.) and detection is performed by addition of either a streptavidin-HRP conjugate or a streptavidin-fluorophore conjugate. This method can be highly sensitive and has been used to detect individual lesions on single DNA molecules (Hirose et al., Photochem. Photobiol. 76:123, 2002; Kim et al., FEBS Lett. 555:611, 2003). However, it is a multi-step method and subject to background from other aldehydes such as carbonyl-modified proteins (Chavez et al., Anal. Chem. 78:6847, 2006). The binding between biotin and streptavidin has high sensitivity and specificity, but streptavidin is bulky and tetravalent, so that binding of a single streptavidin can mask several proximal biotins which can be expected at sites of cluster damage. Direct detection via Fluorescent Aldehyde Reactive Probe ("FARP", 5-(((2-(carbohydrazino)-methyl)thio)acetyl)aminofluorescein, aminooxyacetyl hydrazide (Chakrabarti et al., Int. J. Radiat. Biol. 75: 1055, 1999; Makrigiorgos et al., Int. J. Radiat. Biol. 74:99, 1998)) has been described, which removes the need for a binding step but still requires a washing step, ruling out homogeneous assays, and is subject to lower sensitivity and higher background. FARP probes are available from Invitrogen/Molecular Probes (San Diego, Calif.). A highly creative approach using a fluorescent resonance energy transfer ("FRET") pair of FARP probes was shown to identify clustered damage (Chakrabarti et al., 1999, supra) and might be satisfactory to detect damage without extensive washing. Nonetheless, as yet, no methods let alone commercially available kits for using ARP or FARP probes with intact cells for cell imaging or flow cytometry are available.

Consequently, there is a need for a single sensitive, robust technology that meets the following criteria: (i) detection of a biomarker directly related to radiation exposure, (ii) low background levels from competing markers and reagents employed, (iii) able to detect exposure of at least 2 Gy in <30 minutes, (iv) ability to be adapted to multiple platforms such as lateral flow bioassay, flow cytometry and high throughput clinical analyzers (v) able to be adapted for field use in all environments without the need for refrigeration and minimal user training and (vi) acceptable cost.

SUMMARY OF THE INVENTION

Methods are provided for detecting DNA damage in a subject suspected of having DNA damage wherein the damage results in the formation of aldehyde moieties in DNA comprising the steps of, obtaining a DNA sample from the subject suspected of having DNA damage, combining the DNA sample with a fluorescent or pro-fluorescent, chromogenic or pro-chromogenic hydrazine compound to form a fluorescent DNA or colored DNA by monitoring a fluorescent emission or saturation of color and quantitating the fluorescent emission or color saturation thereby determining the DNA damage in the subject.

In one embodiment of the present invention the DNA damage in the subject is the result of the subject being exposed to ionizing radiation, oxidizing chemicals or any radiation, substance or condition, whether environmental or otherwise, that causes or results in, the formation of aldehyde groups in DNA. The aldehyde moiety may be the result of conversion of a nucleotide base into an aldehyde containing compound. For example, thymidine can be converted by ionizing radiation into 5-formyldeoxyuridine (5-FodU) which contains a free aldehyde that can form a hydrazone bond with a hydrazine compound.

In another embodiment the hydrazine compound can be fluorescent or pro-fluorescent, chromogenic or pro-chromogenic. If the compound is pro-fluorogenic it may be 2-hydrazinoquinoline, 3-methyl-2-benzothiazolinone, 6-hydrazinonicotinamide or 4-hydrazinostilbazole.

In still another embodiment the DNA damage may be detected in a variety of samples including but not limited to isolated DNA, a living or dead cell or a tissue sample.

BRIEF DESCRIPTION OF THE DRAWINGS

These and other features of the invention are described in further detail in the following description and will be better understood with reference to the accompanying drawings, which are briefly described below.

FIG. 4: Derivatization of 5-FodU with phenylhydrazine to form a bis-arylhydrazone.

FIG. 8: Oligonucleotides designed to examine pro-fluorescent detection of 5-FodU in ssDNA and dsDNA, where 5-FodU=U.

DETAILED DESCRIPTION

Figure 1:
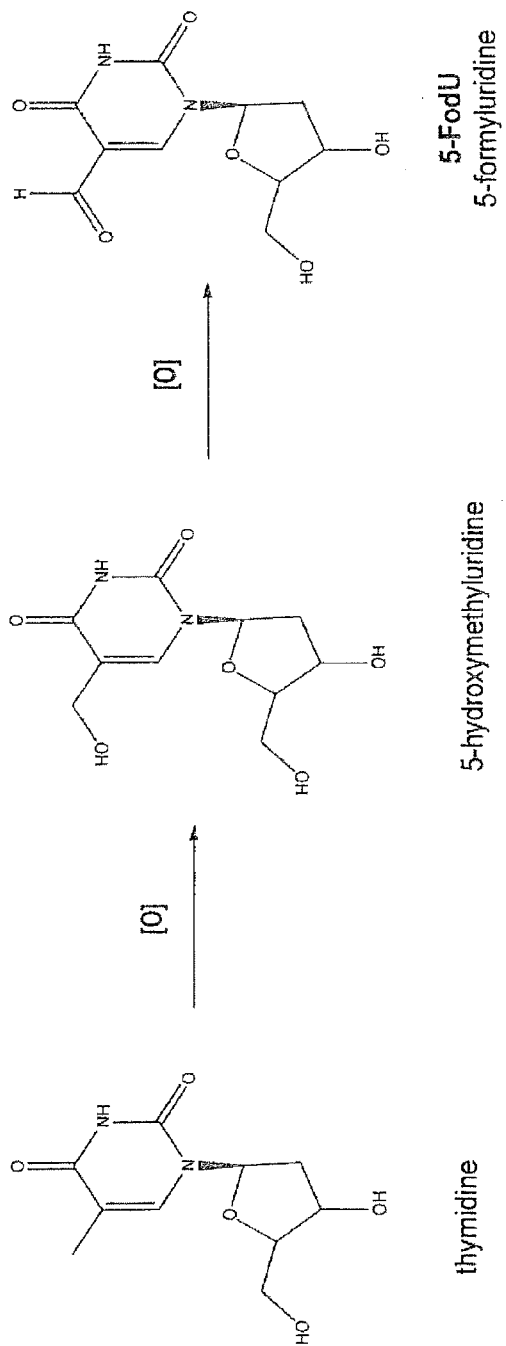
FIG. 1: Two-step mechanism for the conversion of thymidine to 5-formyl-deoxyuridine by oxygen free radicals.

The present invention describes methods and compositions for the detection and quantitation of damage to DNA caused by ionizing radiation, oxidizing chemicals or cellular defects comprising obtaining a biological sample from a subject suspected of being subjected to ionizing radiation, oxidizing chemicals or event resulting in cellular defects, mixing the biological sample with a chromogenic/pro-chromogenic or fluorogenic/pro-fluorogenic hydrazine compound, measuring the chromogenic of fluorogenic signal thereby produced and determining the extent of DNA damage.

To facilitate understanding of the invention set forth in the disclosure that follows, a number of terms are defined below.
Definitions Unless defined otherwise, all terms used herein have the same meaning as are commonly understood by one of skill in the art to which this invention belongs. In the event that there is a plurality of definitions for a term herein, those in this section prevail. All patents, patent applications and publications referred to throughout the disclosure herein are incorporated by reference in their entirety.

The term "aldehyde" as used herein refers to a compound of the formula R—CHO wherein R comprises DNA.

The term "DNA damage" as used herein refers to damage which results in the formation of one or more aldehyde moieties in DNA. For example, ionizing radiation causes conversion of thymidine in DNA to 5-formyldeoxyuridine which contains a free aldehyde group.

The term "hydrazine" as used herein refers to a compound having the formula R—NH—$NH_2$ wherein R is an aromatic moiety. The aromatic moiety may be fluorescent or chromogenic. Alternatively, the aromatic moiety may be pro-fluorescent or pro-chromogenic. The term "pro-fluorescent" as used herein refers to a compound that may be fluorescent but will have a fluorescent signal less than the fluorescent signal of the hydrazone formed when the pro-fluorophore binds to the aldehyde of the damaged DNA. Correspondingly, the pro-fluorophore signal may shift to a higher or lower emission frequency when forming the hydrazone bond with the damaged DNA. The term "pro-chromogenic" as used herein refers to a compound that emits in the visible range and may have little or no color before interacting with the hydrazine compound but will have an enhanced or increased saturation of color upon forming the hydrazone bond with the damaged DNA. Correspondingly, the pro-chromogenic compound may shift in color when forming the hydrazone bond compared to the non-bound state.

The term "ionizing radiation" as used herein refers to any radiation having sufficient energy to cause the formation of an aldehyde moiety in DNA. This includes high energy radiation such as $\alpha$, neutron or $\gamma$ radiation but can include lower energy radiation such as X-ray or ultraviolet radiation as well.

The term "oxidizing chemical" as used herein refers to any compound that is capable of fanning aldehyde moieties within DNA.

The term "sample" as used herein refers to any bodily fluid or tissue sample that may contain DNA. These include living or dead cells, tissue samples, as well as blood or serum, saliva, semen, and the like.

The term "subject" as used herein refers to any animal species such as for example a mammal, a bird, a reptile, an amphibian or a fish. Preferably the animal is a mammal and most preferably a human.

Figure 2:
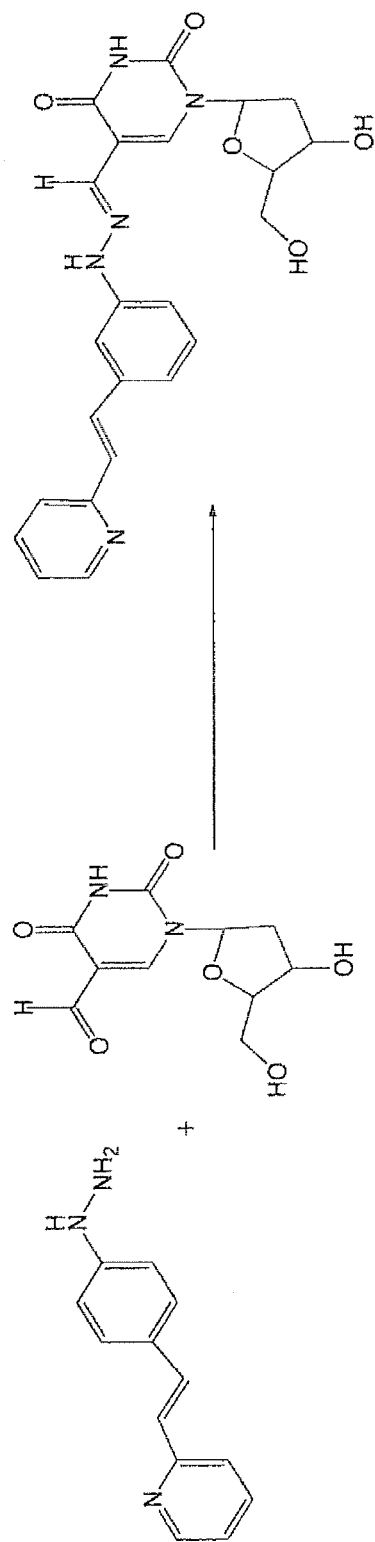
FIG. 2: Expected reaction of the aromatic hydrazine 4-hydrazinostilbazole with 5-FodU to form a fluorescent bis-arylhydrazone.
Figure 3:
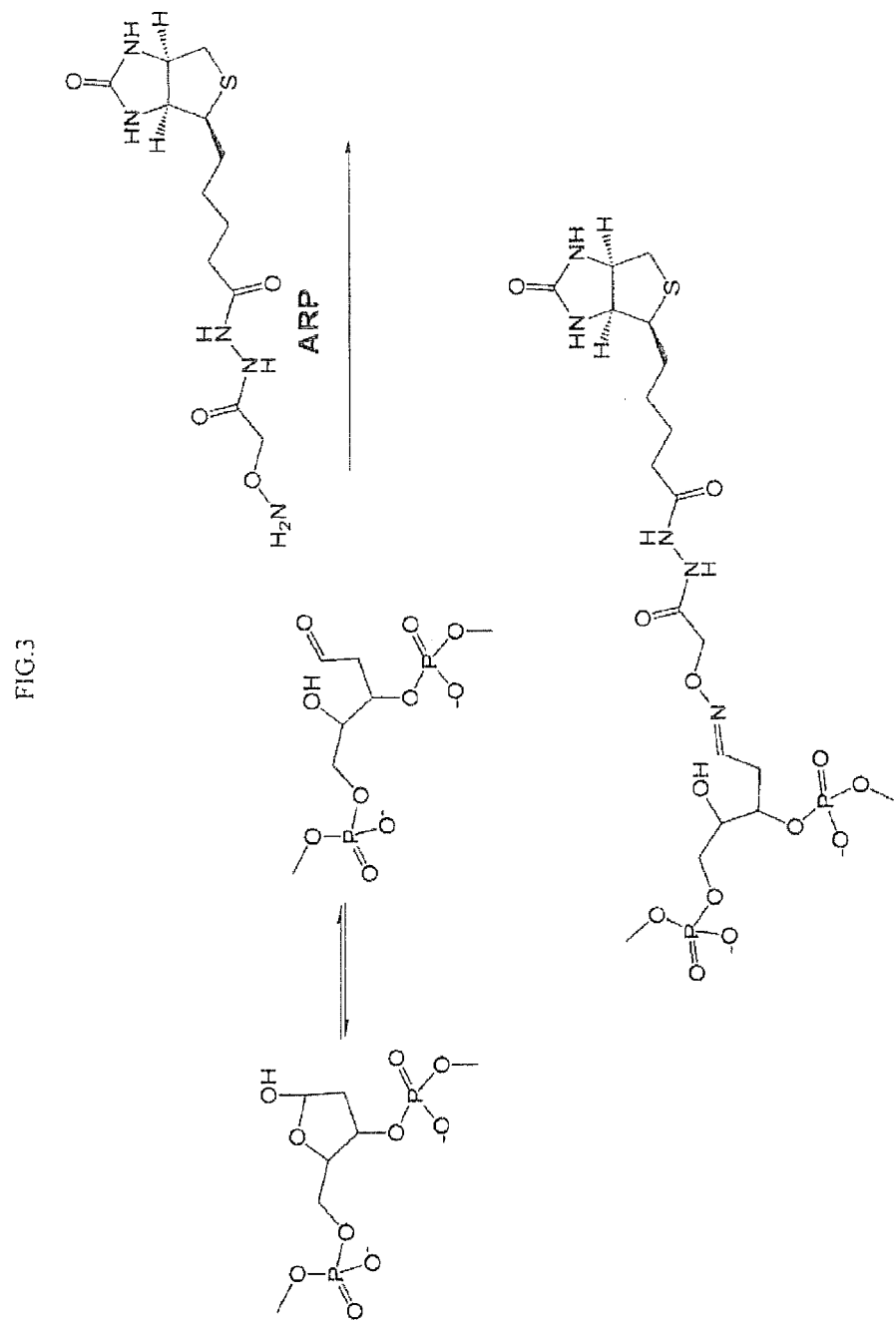
FIG. 3: Scheme for labeling a basic site using the Aldehyde Reactive Probe (ARP).

Radiation, oxidizing chemicals and other events that result in cellular defects often modify DNA and in some instances form reactive groups that are able to interact with a pro-fluorescent/pro-chromogenic aromatic hydrazine to yield a florescent/colored product. Monitoring and quantitating this product can provide information on the extent of DNA modification and correspondingly damage. For example, the weakly blue fluorescent aromatic hydrazine, 4-hydrazino-stilbazole reacts with 5-FodU to form a fluorescent bis-aryl-hydrazone product that absorbs in the orange frequency range (FIG. 2). In addition, this hydrazine has a little or no reactivity with undamaged DNA. This was observed when 0.5 mg/ml undamaged salmon sperm DNA was incubated with 20 µM 4-hydrazino which gave no change in optical properties. However, DNA treated with 9 Gy $\gamma$-radiation yielded a readily visible orange fluorescence with long-wave UV illumination.

DNA oxidation products caused by ionizing radiation: Reactive oxygen species (ROS) and covalent modification of DNA mediate most of the effects of ionizing radiation on biological targets and are responsible for a wide range of health effects including aging and cancer (Cooke et al., FASEB J. 17:1195, 2003; Evans et al., Mutat. Res. 567:1, 2004). The interaction of energetic electromagnetic radiation, or particles, with water yields abundant hydroxyl radicals along with other H atoms and hydrated electrons. Higher energy radiation sheds a correspondingly higher density of radicals along the particle track. Hydroxyl radicals react rapidly with DNA at double bonds, methyl groups and sugar ring carbon atoms yielding radicals that further react with water, oxygen or other targets to cause a wide range of lesions, including strand breaks, abasic sites, modified bases and DNA-DNA or DNA-protein crosslinks. For $\alpha$ particle, neutron or $\gamma$ radiation as might be expected from a radiation accident or nuclear attack, the density of hydroxyl radicals is sufficient to produce numerous double strand breaks and highly clustered damage, with multiple base lesions spread over a few contiguous residues on either strand. Repair of clustered damage can yield additional double strand breaks. While X-rays, $\beta$ particles, ultraviolet light and other less energetic radiation produce fewer double strand breaks, the same free-radical mediated reactions occur but leaving behind widely distributed strand breaks and base adducts.

Hydroxyl radicals and other reactive oxygen species induce patterns of modified bases ((Bjelland and Seeberg, Mutat. Res. 531:37, 2003; Cadet et al., J. Environ. Pathol. Toxicol. Oncol. 23:33, 2004; Cadet et al., Mutat. Res. 424:9, 1999; Cadet et al., 2003, supra). These might be considered potential signatures of radiation exposure. Among the best characterized oxidized bases is the mutagenic base 8-oxoguanine (8-oxodG (David et al., Nature 447:941, 2007)), the abundance of which has been used as an indirect measure of oxidative damage. Exposure of thymine in the context of DNA, or as a free nitrogenous base, nucleoside or nucleotide to hydroxyl radicals in the presence of oxygen, can yield 5-FodU as a prominent product (FIG. 1, (Bjelland et al., Mutat. Res. 486:147, 2001; Bjelland et al., Biochemistry, 34:14758, 1995; Liu et al., DNA Repair 2:199, 2003)). 5-FodU is produced with similar abundance to 8-oxodG after $^{60}$Co irradiation, as first described by Kasai et al. (Mutat. Res. 243:249) in 1990. Chemical oxidants such as peroxide or iron based Fenton reagents can also readily oxidize the 5-methyl group of thymine to 5-FodU. 5-FodU is a common adduct in chromosomal DNA after radiation exposure, but given the size of nucleotide pools, a significant source of 5-FodU in both DNA and RNA is likely via oxidation of free thymine. Ionizing radiation may result in accumulation of 5-formyl deoxyuridine triphosphate ("5-FodUTP") and incorporation during chromosomal replication and/or repair synthesis (Klungland et al., Toxicol. Lett. 119:71, 2001). In the context of DNA, 5-FodU is weakly mutagenic, and presumably mediates some of the carcinogenic effects of ionizing radiation. Indeed, 5-FodUTP induces both transition and transversion mutations in cells, presumably via misincorporation and/or mispairing during replication.

Toxicity, mutagenicity and repair of 5-formyldeoxyuridine: Like other common forms of oxidative damage, the accumulation of 5-FodU in DNA after exposure to ionizing radiation can mediate toxic effects by several means. Extensive literature exists describing the contribution by 5-FodU to the mutagenicity of ROS. The results conclude that the formyl moiety significantly lowers the pKa of uridine from 9.4 to 6.8 due to the electron withdrawing properties of the formyl moiety (Privat and Sowers, Mutat. Res. 354:151, 1996). It is this lowered pKa that results in enhanced mispairing (FIG. 2) of the ionized form with guanine during DNA replication and demonstrates the mutagenicity of 5-FodU. Kamiya (Kamiya et al., Mutat. Res. 513:213, 2002) reported T→G and T→A transversions by 5-FodU in mammalian cells by incorporating 5-FodU in predetermined sites in double-stranded vectors.

The molecular basis of the mutagenicity of 5-FodU oligonucleotides containing 5-FodU was observed by Ono et al., Chem. Pharm. Bull. 42:2231, 1994. Synthetic methods of preparing the protected 5-FodU phosphoramidites and their incorporation into oligonucleotides are well described, (e.g. Berthod et al., Nucleosides & Nucleotides 15:1287, 1996). Studies of the melting behavior of oligonucleotides incorporating 5-FodU moieties demonstrated that 5-FodU-A base pair are less stable than the T-A base pair. DNA replication studies on a template-primer system showed that dATP was incorporated into the DNA strand at the site opposite 5-FodU by Klenow DNA polymerase, but at a reduced rate (Ono et al., 1994, supra). In a subsequent investigation Karino et al., (Nucleic Acid Res. 29:256, 2001) synthesized 5-FodC oligonucleotides and showed (i) that 5-FodC:A, 5-FodC:C or 5-FodC T base pairs significantly reduce the Tin's and (ii) insertion of dGMP opposite 5-FodC appears to be less efficient relative to insertion opposite 5-methyl-cytidine and (iii) dAMP and dTMP are misincorporated more frequently opposite 5-FodC than 5-methyl-cytidine. It was suggested that 5-FodC may induce the transition mutation C:G→T:A and the transverse mutation C:G→A:T during DNA synthesis.

The major defense against these effects is by base excision repair, whereby 5-FodU is recognized by DNA repair enzymes that serve to restore the base to deoxythymidine. *E coli* repair 5-FodU with the Nth, Nei and MutM base excision repair proteins by removal of the base by N-glycosylase to create an abasic (AP) site followed by nicking of the damaged DNA strand upstream, thus creating a 3'-OH terminus (Zhang et al., J. Biol. Chem. 275:35471, 2000). In budding yeast, the Ntg1 and Ntg2 serve as the 5-formyluracil deglycosylases and AP lyases, leaving a nick adjacent to the position of the oxidized base (Zhang et al., Int. J. Radiat. Biol. 79:341, 2003). Similarly, human cells express hNTH1 and hNEIL1 deglycosylase/AP lyases that remove 5-FodU from artificial substrates and nick the DNA (Matsubara et al., Biochemistry 42:4993, 2003; Miyabe et al., Nucleic Acids Res. 30:3443, 2002; Zhang et al., DNA Repair 4:71, 2005).

Radiation dose and injury: Although nearly all radiation injuries since the bombing of Hiroshima and Nagasaki have been due to accidents, recent interest has focused on the potential for intentional detonation of nuclear or radiologic devices. While the much discussed radiologic dispersal devices (dirty bombs) would probably cause a limited number of casualties, detonation of improvised nuclear devices or nuclear weapons would result in mass casualties. Individuals in the immediate vicinity of a nuclear explosion would likely suffer lethal thermal burn or blast injuries in combination with radiation exposure, but many other victims are expected to suffer radiation exposures alone or along with otherwise treatable burn and trauma injuries (the combined injury syndrome). In the event of a nuclear detonation, it will be imperative to readily detect the level of radiation exposure to soldiers and/or civilians. For military personnel, it will be important to determine whether they must be removed from further exposure or can be sent back into harm's way and for civilians, it will be important to triage victims into treatable and untreatable groups.

Currently, employees working in proximity to nuclear reactors or instruments and/or protocols that use radioactivity such as X-ray machines wear one of two types of badge dosimeters. They are X-ray film-based dosimeters or thermoluminescent-based dosimeters. Unfortunately, this does not provide immediate real time detection of DNA damage. Such badges cannot be quickly scanned to identify the extent of potential DNA damage.

Figure 10:
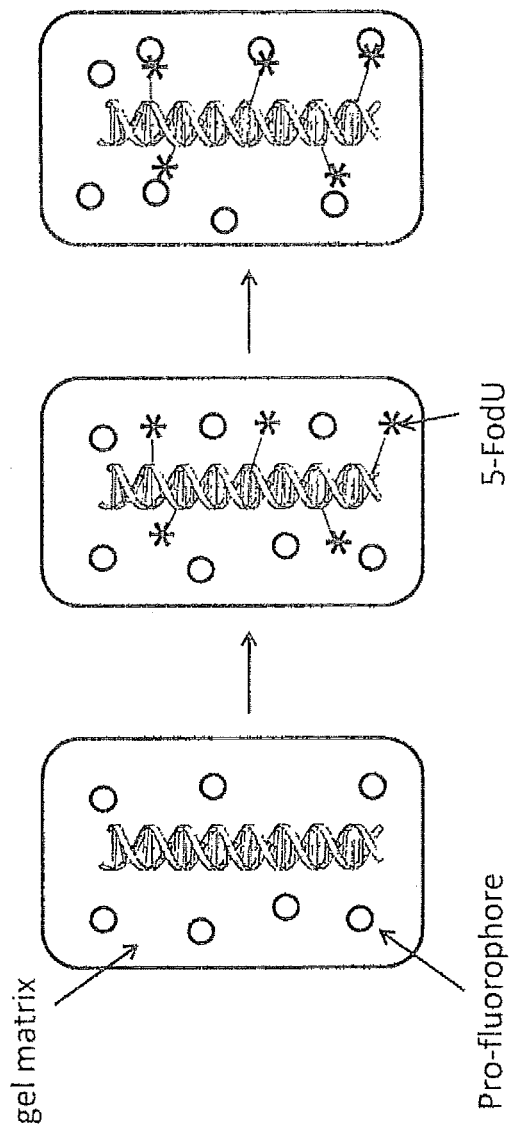
FIG. 10: Diagrammatic representation of pro-fluorophore binding to 5-FodU and fluorescent emission.

The present invention provides a real time biomimetic dosimeter comprised of a packet, or other enclosure, in a badge-type format that contains purified DNA, or preferably poly-T DNA, combined in a matrix with a pro-fluorescent aromatic hydrazine that on exposure to ionizing radiation converts the thymidine bases within the DNA to 5-formyl-deoxyuridine (5-FodU). Since 5-FodU reacts with the aromatic hydrazines forming a fluorescent bis-arylhydrazone as described above, the fluorescent product can be detected using a fluorescence reader (FIG. 10). As the quantity of 5-FodU produced is proportional to the amount of exposure to ionizing radiation the fluorescence level similarly quantifies the exposure. This badge unlike the X-ray film based dosimeter can be re-used following reading. For example, by recording the amount of radiation damage from an initial exposure, that recorded exposure can be utilized as the baseline for the next determination of damage in a subsequent exposure.

Responses to whole body irradiation: Acute radiation syndrome ("ARS") is a multi-organ stress response that occurs after whole-body or significant partial-body irradiation of greater than 1 Gy delivered at a relatively high dose rate (Dainiak et al., Hematology Am. Soc. Hematol. Educ. Program 473, 2003; Goans and Waselenko, Health Phys. 89:505, 2005; Jackson et al., RJR Suppl. 27:161, 2005; Waselenko et al., Ann. Intern. Med. 140:1037, 2004; Weisdorf et al., Biol. Blood Marrow Transplant 12:672, 2006, see Table 1, Dose Response in ARS). The most replicative cells are the most sensitive to the acute effects of radiation, including the bone marrow and intestinal epithelial precursors, but other tissues display significant sensitivities as well. The clinical manifestation of ARS is dose-dependent, reflecting a combination of hematopoietic, gastrointestinal, and cerebrovascular syndromes. Symptoms of acute radiation are dependent on the absorbed dose and may appear within hours to days, but follow a characteristic sequence. Patients with a total body exposure of >1 Gy will develop dose dependent, increasingly severe aspects of the hematopoietic syndrome. Because bone marrow progenitors are unable to divide after exposure of 2 to 3 Gy, a hematologic crisis may ensue, characterized by pancytopenia, infection, bleeding, and poor wound healing. Lymphocyte depression is maximal at two weeks, and may take several months to recover. Time to nadir is inversely proportional to dose, and depth and duration are proportional to dose. Platelet production decreases and slowly recovers, leading to a period of thrombocytopenia. Neutrophils serve a major role in innate immunity and typically comprise 70% of circulating leukocytes, totaling 2,500-7,500 cells/µl and neutropenia below 1000 cells/µl strongly predisposes to infection. Neutropenia develops over the first week and full recovery may take several months. To head off sepsis, treatment with granulocyte colony stimulating factors to restore neutrophil numbers along with broad-spectrum prophylactic antimicrobial agents is considered standard therapy during the neutropenic period.

At doses of 3.5 Gy or higher, the increasing damage to other organs gains greater significance. The breakdown of the intestinal mucosal barrier results in abdominal pain, diarrhea, nausea and vomiting, and predisposes patients to bowel obstruction, gastrointestinal bleeding, and infection. Systemic effects may include malabsorption resulting in malnutrition, dehydration, electrolyte imbalance, and acute renal failure. Loss of intestinal epithelial integrity enhances the hematopoietic syndrome as inflammation depletes neutrophils and leakage of bacteria promotes local infection and significantly enhances the likelihood of sepsis. The lungs are another survival limiting organ target. Acute radiation pneumonitis develops two to six months after exposure and is manifested by cough, dyspnea, and respiratory difficulties. Progressive and irreversible pulmonary fibrosis may develop even if the patient initially was asymptomatic. Survival becomes less likely with increasing dose and victims exposed to 10 Gy suffer rapid, multi-organ failure, a situation incompatible with long-term survival.

TABLE 1

| Dose, Gy | Prodrome | Manifestation of illness | Prognosis without therapy |
| --- | --- | --- | --- |
| 0.5-1.0 | Mild | Slight decrease in blood cell counts | Survival with cancer risk |
| 1.0-2.0 | Mild to moderate | Early signs of bone marrow damage | Survival likely (~90%) with cancer risk |
| 2.0-3.5 | Moderate | Moderate to severe bone marrow damage | Survival expected if bone marrow recovers |
| 3.5-5.5 | Severe | Severe bone marrow damage; slight GI damage | Death expected within 3.5-6 wk (>50% lethality) |
| 5.5-7.5 | Severe | Pancytopenia and moderate GI damage | Death probable within 2-3 wk, few long-term survivors |
| 7.5-10.0 | Severe | Marked GI and bone marrow damage | Death probable within 1-2 wk, no long-term survivors |
| 10.0-20.0 | Severe | Severe GI damage, pneumonitis, cognitive loss | Death certain within 5-12 d |
| 20.0-30.0 | Severe | Cerebrovascular collapse, fever, shock | Death certain within 2-5 d |

There are several other time points and locations where it is critical to be able to determine the level of exposure to radiation including (i) immediately following exposure for triage at medical centers, (ii) high throughput quantitative laboratory tests that could perform up to 200,000 tests/week, (iii) rapid dose quantification in the field for daily, weekly and monthly monitoring following a nuclear event and (iv) a test with high levels of accuracy over a range of 0.01-20 Gy for post event follow-up of patients.

Hydrazines (R—$NHNH_2$) form stable hydrazones with aldehydes (R—CHO) in organic media but in aqueous media the hydrazones are in equilibrium unless both the hydrazine and the aldehyde components are aromatic. Kaneko (Kaneko et al. Bioconj. Chem. 2:133, 1991) in a thorough study showed the aqueous stabilities of a variety of hydrazones in their search for an acid labile hydrazone for the endosomal release of doxorubicin conjugated to antibodies. Ono (Ono et al., 1994, supra) demonstrated that a decameric oligonucleotide with a single 5-FodU that was reacted with phenylhydrazine quickly and quantitatively formed a stable his-arylhydrazone, yielding a characteristic absorbance at 420 nm (FIG. 4).

Design of a 5-FodU-based chemical detection method for oxidative DNA damage: The pro-chromogenic/pro-fluorescent technology to detect 5-FodU damage provides the following advantages: (i) the reaction proceeds in biological media, i.e. PBS yielding a stable chromogenic/fluorogenic product wherein 5-FodU is a component of the product; (ii) favorable kinetics of reactivity between 5-FodU and the pro-fluorescent aromatic hydrazine catalyzed by aniline; (iii) limited steric encumbrance following covalent linking of the pro-fluorescent aromatic hydrazine to 5-FodU; (iv) a basis for a homogeneous assay i.e. an assay in which a washing step is not required; (v) a basis for a assay high throughput assay that can be incorporated into existing instrumentation; (vi) low limits of detection and an extended linear range; (vii) a basis for use in multiple platforms such as immunohistochemistry, flow cytometry and ELISA and (viii) a field test assay such as a "dipstick" test requiring minimal technical training.

Figure 5:
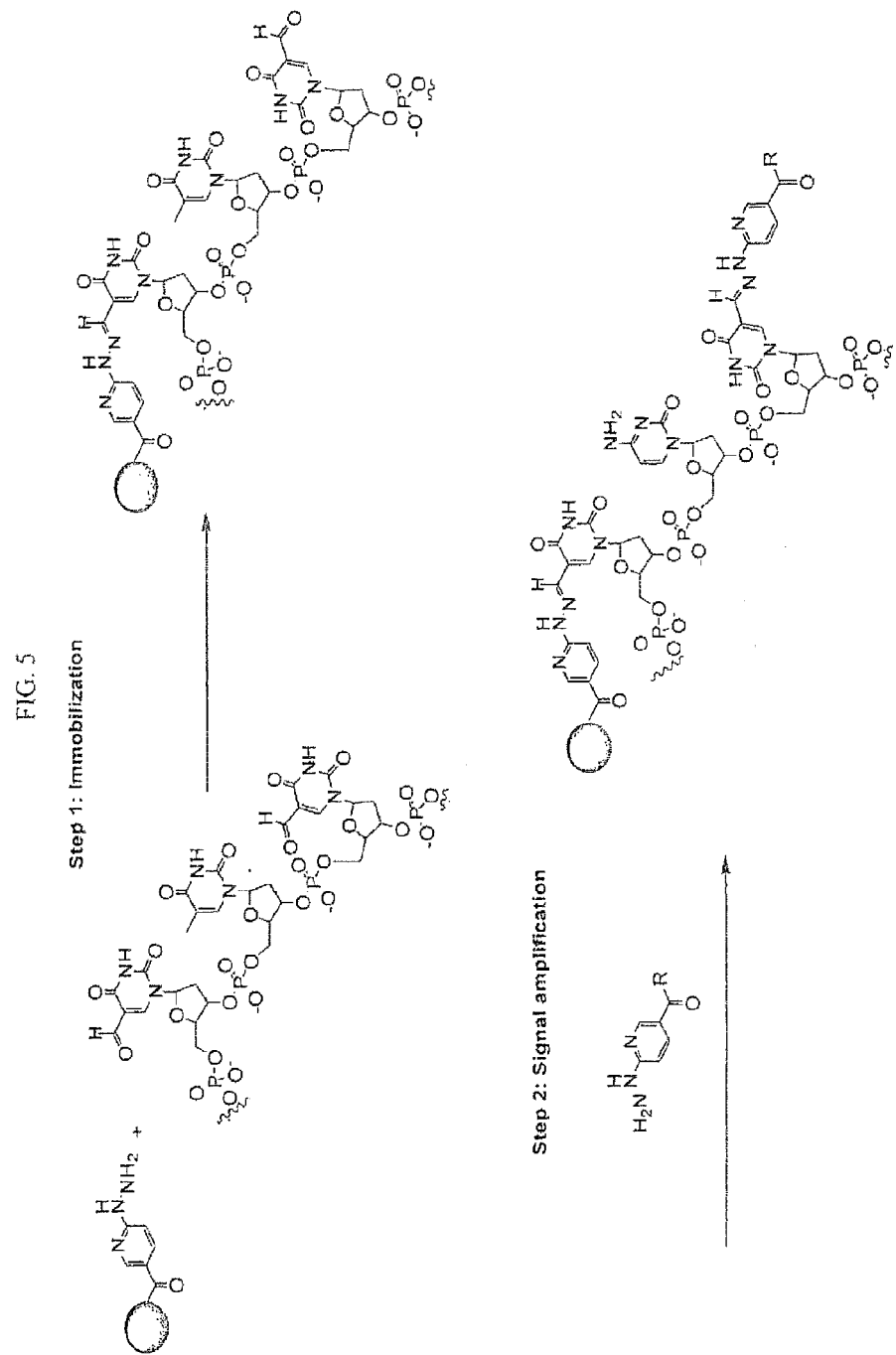
FIG. 5: Schematic representation of the chromogenic/fluorogenic assay wherein 5-FodU-modified DNA (B) is immobilized on aromatic hydrazine beads (A) to concentrate the 5-FodU DNA by immobilization in Step 1 (C) followed by addition of pro-chromogenic/pro-fluorescent aromatic hydrazine in Step 2 to produce a chromogenic or fluorescent signal (D).

Chromogenic/fluorogenic assay: FIG. 5 is a schematic depiction of the assay wherein 5-FodU-modified DNA is concentrated by immobilization on a pro-fluorescent aromatic hydrazine bead, a zone on a lateral flow strip or the tip of a fiber optic cable. Subsequently, solution phase pro-fluorescent aromatic hydrazine is added to react with the remaining 5-FodU moieties thereby increasing the signal. A library of aromatic hydrazines can be prepared and their absorbance and fluorescent properties determine to select one or more with the optimal properties for the detection of 5-FodU in the desired assay.

The chromogenic assay is adaptable to a rapid self-assessment assay to determine radiation exposure over 2 Gy. Since this assay does not employ any biological reagents and the signal is visual, it satisfies all the requirements for functionality in adverse conditions, convenience of use, shelf-life and ease of manufacturing. The fluorogenic assay in association with a portable fluorescent reader is adaptable to determining levels of radiation and usable under adverse conditions. Furthermore, the fluorogenic assay is readily adaptable to high-throughput assays in a laboratory environment based on fluorescent multi-plate robotic instruments or flow cytometry.

qPCR-Based Assay a quantitative polymerase chain reaction ("qPCR") based assay using the following multi-step protocol can be performed robotically, (e.g. Kingfisher (ThermoFisher) multiwell magnetic bead robot Pittsburgh, Pa.). Such an assay would include the following steps:

1.) obtain a blood sample or tissue sample of interest is treated to lyse cells to expose 5-FodU-containing DNA;

2.) add aromatic-hydrazine-coated magnetic beads and aniline-containing buffers to the sample to capture the 5-FodU-modified DNA;

3.) wash the beads;

4.) add all the components required to perform qPCR analyses which may additionally include random primers or a mixture of primers to human sequences that are known to have multiple copies in the human genome; and 5.) perform qPCR and tabulate the results for analysis.

The high sensitivity of a qPCR-based assay will allow inspection of samples from non-invasive sources such as hair, sputum and urine. It is known that DNA fragments are present in urine (transrenal DNA) and have been used as biomarkers of diseases which can be detected by PCR.

EXAMPLES

Example 1

Pro-Fluorescent Detection of 5-FodU

Figure 6:
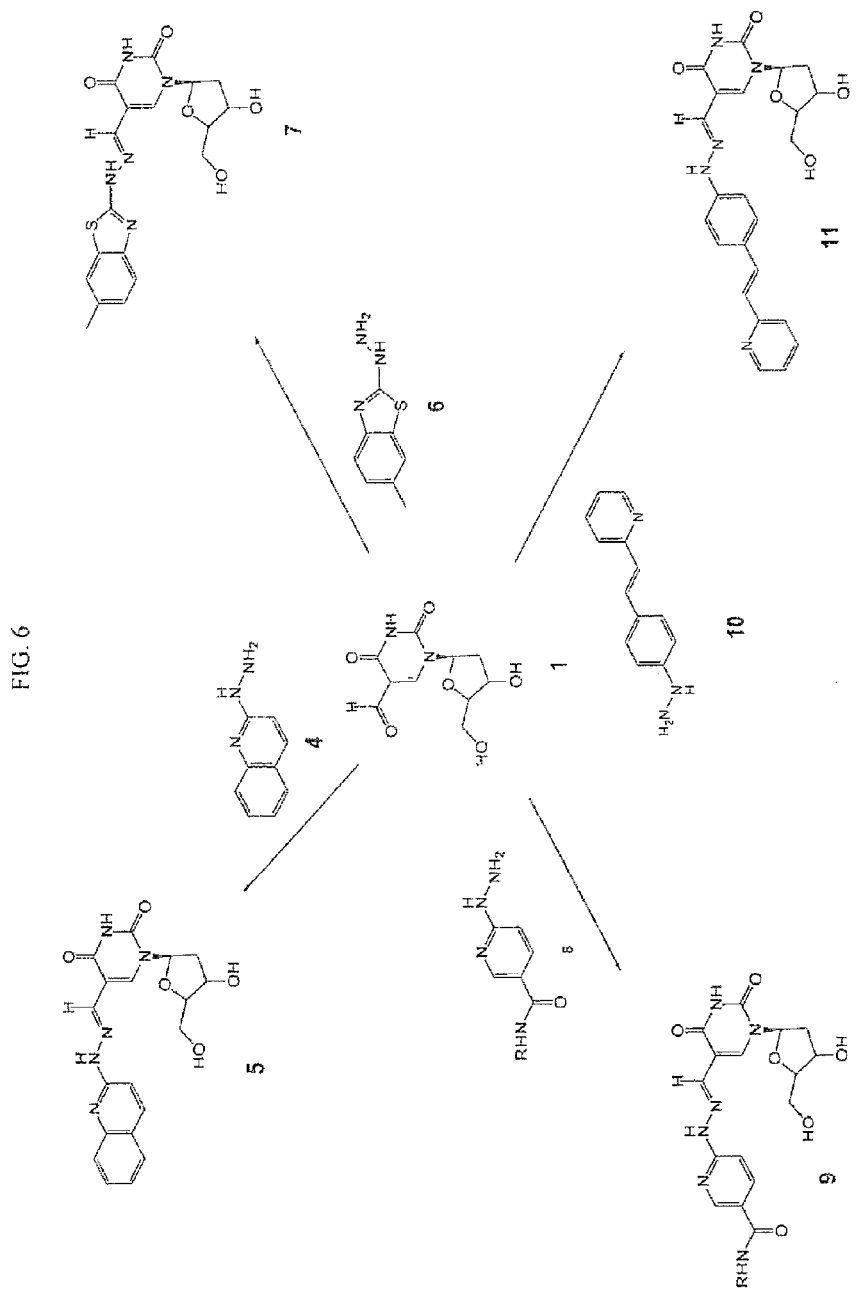
FIG. 6: Initial group of reactions with 5-FodU (1) to form fluorescent hydrazones (5, 7, 9 and 11) to be prepared from commercially available aromatic hydrazines, 2-hydrazinquinoquinoline (4), 3-methyl-2-benzothiazolinone hydrazone ("MBTH") (6), 6-hydrazinonicotinamide (8) and 4-hydrazinostibazole (10).

5-FodU is synthesized as described in the literature. 5-Di-O-acetyl-thymidine is oxidized to di-O-acetyl-5-formyl-deoxyuridine by $CuSO_4/K_2S_2O_8$/2,6-lutidine/aqueous acetonitrile/65° C./2 hours in ~52% yield as described by Ono et al., 1994, supra. De-acetylation using aqueous acetic acid yields 5-FodU which is then condensed with a variety of structurally diverse commercially available hydrazines as shown in FIG. 6. Reaction kinetics are examined with and without 10-100 mM aniline and with respect to pH, temperature, etc. The hydrazones are then isolated and their structures confirmed by $^1H$ nuclear magnetic resonance ("$^1H$ NMR") and mass spectroscopy. The fluorescent properties of this panel of 5-FodU hydrazones are evaluated with respect to their absorbance and emission wavelength, quantum yields and photostability.

Figure 7:
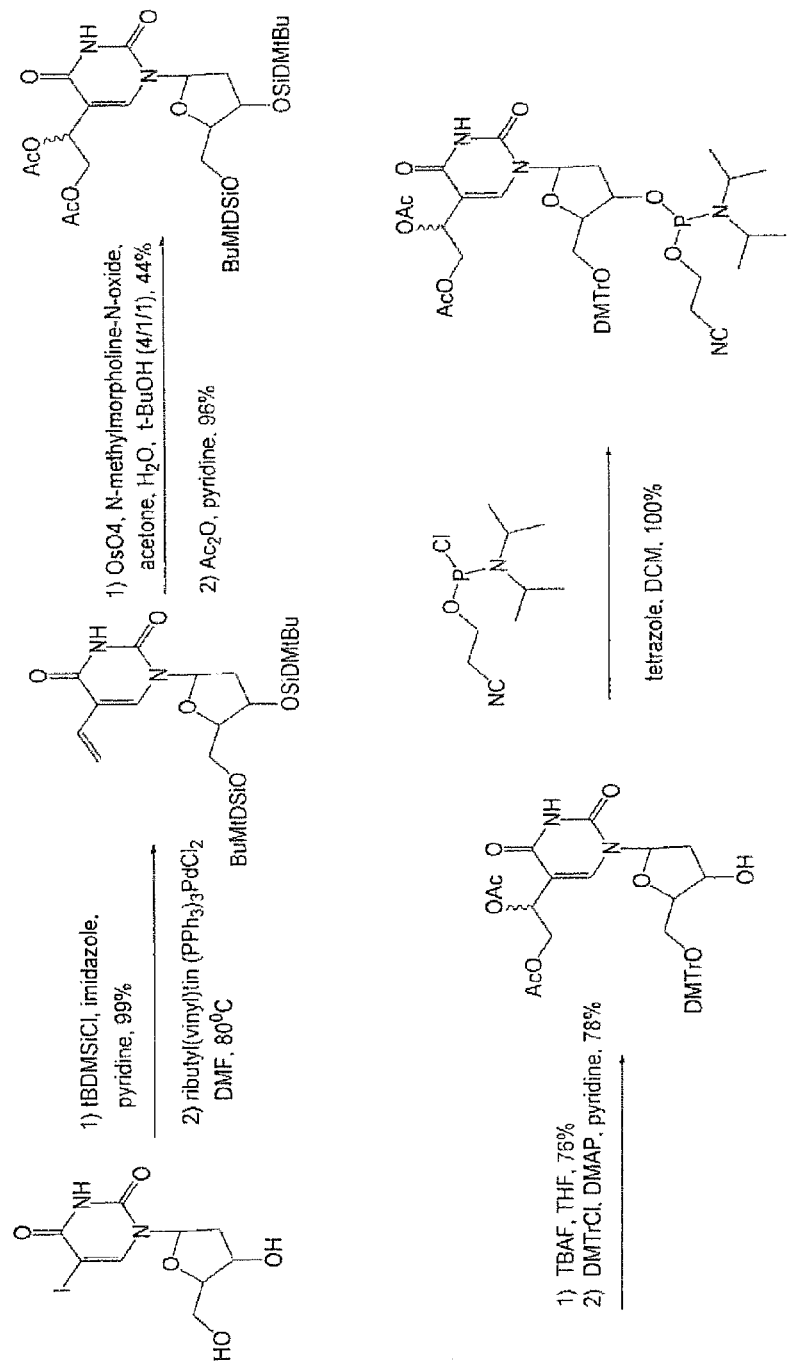
FIG. 7: Scheme for the synthesis of 5-FodU phosphoramidites as described by Sugiyama (Zhang et al. Nucleic Acids Res. 25:3969, 1997).

Oligonucleotides are prepared bearing 5-FodU moieties. Sugiyama (Zhang et al., Nucleic Acids Res. 25:3969, 1997) described the synthesis of a protected 5-(1-2)-di-O-acetoxyethyl)-2-deoxyuracil phosphoramidite (FIG. 7). All intermediates synthesized are characterized by $^1$H NMR and mass spectroscopy. 5-FodU substituted oligonucleotides are ultimately isolated by periodate oxidation of the 5-(1,2-dihydroxy)-deoxyuracil-containing oligonucleotides. PAGE gel and mass spectral data are obtained for all oligonucleotides synthesized. Oligonucleotides are synthesized with single and multiple 5-FodU moieties (FIG. 8), as a model for dispersed and clustered damage. Complementary oligonucleotides with A or G opposite the 5-FodU sites are synthesized to determine how the 5-FodU base-pairing alters reactivity. The single stranded and double stranded oligonucleotides are treated with aromatic hydrazines including 2-hydrazinoquinoline, 3-Methyl-2-benzothiazolinone hydrazone, 6-hydrazinonicotinamide, 4-hydrazinostilbazole and the adducts are evaluated to examine the effects on extinction coefficient and fluorescent characteristics of the hydrazones. The products are analyzed by gel electrophoresis, mass spectrometry and fluorescence.

Comparison of A, B, and C (FIG. 8) reveal the overall impact on Tm of the unmodified oligonucleotide vs. a modification near the end vs. a modification in the middle. It will also allow comparison of fluorescent signal when the fluorophore is located at the end vs. the middle of the oligonucleotide. Comparison of C, D, E, and F (FIG. 8) reveals the extent of fluorophore-fluorophore interactions (positive or negative) for in-phase versus out-of-phase positions, and distance-dependence (10 bp vs. 20 bp apart) of in-phase fluorophore-fluorophore interactions. Comparison of B and F vs. G (FIG. 8) reveals if the center fluorophore can bridge between the two end fluorophores to yield a greater signal or greater quenching. Comparison of C and G vs. H (FIG. 8) reveals extent of the interaction of multiple, maximally-separated fluorophores to closely-clumped fluorophores, relative to the single center fluorophore. Tm and background fluorescent signal determinations can be observed from evaluation of control oligonucleotide I.

5-FodU triphosphate is synthesized by chemical means (Armstrong et al., Biochemistry 15:2086, 1976). 5-FodUTP is doped into polymerase chain reaction ("PCR") amplification reactions at increasing percentages and the level of incorporation determined. Several methods to detect 5-FodU in PCR products are utilized including gas chromatography/ mass spectroscopy ("GC/MS") (Douki et al., Chem. Res. Toxicol. 9:1145, 1996), using the synthesized 5-FodU as a standard. In addition, the PCR products are reacted with Aldehyde Reactive Probe (ARP, N-(aminooxyacetyl)-N'-(D-biotinoyl) hydrazine) before and after treatment with deglycosylating enzymes or incubation at 100° C. to form abasic sites, to determine reactivity of 5-FodU vs. abasic sites to this probe. Biotin incorporation from ARP is examined by BABA assay and/or FluoReporter Biotin Quantitation Assay (Invitrogen, San Diego) to determine sensitivity and specificity as a reference. Fluorescent hydroxylamine ("FARP") reagents, such as Alexa Fluor 488 hydroxylamine (Invitrogen, San Diego), are also examined for sensitivity and specificity. Then, the 5-FodU labeled amplicons is reacted with pro-fluorophore hydrazines including 2-hydrazinoquinoline, 3-methyl-2-benzothiazolinone hydrazone, 6-hydrazinonicotinamide, and 4-hydrazinostilbazole and the fluorescence of the products is quantified and the results correlated with the digestion results. The efficiency and kinetics of fluorescent labels are examined with respect to such variables as pH and temperature. In addition, the minimum detectable level of 5-FodU that can be detected by the pro-fluorophore technology is determined.

Example 2

Detect 5-FodU in Irradiated Chromosomal DNA

1. Preparation and irradiation of purified chromosomal DNA and detection of 5-FodU: Salmon sperm DNA is dissolved in water at >10 mg/ml. 10.0 mg aliquots are diluted to 0.5 mg/ml and subjected to irradiation in a $^{60}$Co source (~1.5 Gy/min) to obtain doses of e.g. 0, 0.1, 0.2, 0.4. 0.8 . . . 3.2, 6.4 and 12.8 Gy, to cover the full range of physiologically relevant doses.

2. Detection of formation of 5-FodU: Detection of 5-FodU by ionizing radiation, is determined by established methods using GC-MS or HPLC-MS/MS (e.g. (Cadet et al., Free Radic. Biol. Med. 33:441, 2002; Douki et al., 1996, supra; Hong and Wang, Anal. Chem. 79:322, 2007)). Chemically synthesized 5-FodU, 5-FodUTP and 5-FodU containing oligonucleotides are utilized to develop methods and provide calibration standards. Then, the irradiated DNA is reacted ARP as described above, to examine sensitivity and specificity of detection. Using the optimal conditions identified above, the irradiated DNA is treated with pro-fluorophore hydrazines including 2-hydrazinoquinoline, 3-methyl-2-benzothiazolinone hydrazone, 6-hydrazinonicotinamide, and 4-hydrazinostilbazole. The fluorescence enhancement, Stokes shift and reaction kinetics is quantified and the results correlated with the ARP probe and the GC-MS results.

Example 3

Detect 5-FodU in Tissue Culture Cells and Paraffin-Embedded Tissue

1. Analysis of DNA oxidation in tissue culture cells: Controls are screened for background reactivity for the pro-fluorophore hydrazines including 2-hydrazinoquinoline, 3-methyl-2-benzothiazolinone hydrazone, 6-hydrazinonicotinamide, and 4-hydrazinostilbazole, with and without 100 mM aniline, and compare them to the commercially available reagents including ARP and FARP (Invitrogen, San Diego, Calif.), anti-8-OxodG antibody and the OxyDNA and/or OxyFLOW kits (Biotrin, Dublin, Ireland, HemoGenix, Colorado Springs, Colo.). Adherent cells, A549 (lung), MCF-7 (breast), SCC6I (head and neck) and non-adherent HL60 (PML) and K562 (CML) tumor cell lines, are wash, permeabilized and fixed with paraformaldehyde, and then wash in PBS. The adherent lines are used for imaging and the non-adherent lines are used for flow cytometry and multi-well fluorimetry. Reagents are added; the cells are incubated, washed with PBS and screened by fluorescence imaging, flow cytometry and/or 96 well plate fluorimetry. To induce free radical damage in the fixed tissue culture cells, the cells are treated with a mixture of 100 μM $FeSO_4$ and 100 μM $H_2O_2$ for 0, 10, 30 and 60 minutes and then repeat the analysis to detect enhanced reaction with pro-fluorophore hydrazines and the commercial alternatives ARP, FARP, anti-8-OxodG antibody and the OxyDNA and/or OxyFLOW kits.

The adherent cells are stained with a DNA counterstain (e.g. Syber Green) and examined by microscopy to determine whether the fluorescent product demonstrates localization, primarily or exclusively to the nucleus. The highest intensity of fluorescence is in the nucleus following treatment with hydroxyl radicals. The aromatic hydrazines are specific to aromatic aldehydes. Thus fluorescence is low and nuclear localized in the controls and restricted to nucleic acids in oxidized cells. Cytoplasmic staining is due primarily to oxidized ribonucleic acid ("RNA"). Consequently cells were treated with RNAse prior to staining.

2. Analysis of oxidative damage in living cells: To induce intracellular hydroxyl radicals in tissue culture cells, the cells are treated with 100 µM $FeSO_4$ for 1 hour, to allow iron uptake, and then with 100 $H_2O_2$ to induce the Fenton reaction and produce hydroxyl radicals (Ishii et al., Cell Calcium 39:487, 2006). Control cells are pre-incubated with hydroxyl radical scavengers, 5 mM N-(2-mercaptopropionyl)-glycine ("MPG") and 20 mM 1,3-dimethyl-2-thiourea ("DMTU"), or $Fe^{2+}$ chelator, 100 µM 2,2'-dipyridyl ("DP"), to block hydroxyl radical damage. At time points of 0, 10, 30, 60 and 120 minutes, the cells are washed, permeabilized and fixed with paraformaldehyde, and then wash in PBS to assess oxidative damage to chromosomal DNA. As an alternative source of hydroxyl radical, cells are irradiated in the $^{60}Co$ irradiator at doses of 0 to 50 Gy. Aliquots of ~$10^6$ cells are removed from each sample for DNA extraction and conventional analysis of oxidative damage by GC/MS. The 5-FodU content and kinetics of removal from DNA are then determined. For staining, cells are fixed with paraformaldehyde. An aliquot is stained with FARP, anti-8-OxodG antibody and the OxyDNA and/or OxyFLOW kits using manufacturer's protocols, and analyzed by quantitative imaging and flow cytometry. The 5-FodU is then detected in the pro-fluorophore probes by examining each with and without aniline to accelerate kinetics. In this experiment the reagents are added, incubated, washed and signal detected using fluorimetry, quantitative imaging, and/or flow cytometry to develop plots of fluorescence enhancement vs. incubation time. Data is obtained to determine sensitivity and linearity and to compare performance to FARP, anti-8-OxodG and the OxyDNA/OxyFLOW kits. From these experiments, the relative sensitivity and specificity are evaluated for the of aromatic hydrazine pro-fluorescence detection compared to commercial reagents.

The ability to detect physiological, environmental and drug-induced levels of oxidative damage, the effects of hypoxia, TNF-alpha, $Zn^{2+}$, paraquat, and other well known inducers of mitochondrially derived ROS and hydroxyl radicals, on level of staining by pro-fluorophores and commercial reagents is determined. Microscopy, multi-well scanning and flow cytometry are used to develop dose response curves and document the effects of well-described antioxidant drugs such as n-acetyl cysteine, glutathione, butylated hydroxyanisole ("BHA"), butylated hydroxytoluene ("BHT"), etc. on oxidative damage. The evidence collected for the replacement of conventional laboratory assays of oxidative damage and antioxidant effects with pro-fluorescence assays is positive. Using the pro-fluorophore aromatic hydrazines as direct stains without a washing step may also be used.

3. Analysis of fixed and embedded tissue: Paraffin blocks in which human tumor cell lines are grown as xenograft tumors in athymic nude mice have been embedded are utilized. These imbedded tissues are obtained from, Dr. Ralph Weichselbaum (University of Chicago Medical Center, Chicago, Ill.) who has an extensive range of relevant tumors in blocks, including examples treated with radiation and/or chemotherapeutic agents and others treated with TNFalpha, which might be expected to display elevated levels of oxidative damage over the tumors alone.

Sections are prepared by placing them onto slides for conventional H & E analysis. Background binding is determined by treating the sections with pro-fluorophore hydrazines with and without aniline. The reagents are added, and the slides are incubated, washed and assayed by fluorescence microscopy to detecting damage in situ. Sections of fixed and embedded tissue are examined using FARP, anti-8-OxodG antibodies, or the OxyDNA kit and compared to staining with pro-fluorophore reagents. The sections are then subjected to fluorescence microscopy, counterstaining with a DNA stain to detect nuclei, and examined to identify localization and sensitivity of staining. Tumor cells are examined and their staining compared to staining of the surrounding stroma and normal tissue. Pro-fluorescence reagents displayed a particularly significant fluorescent signals in these applications. Background binding of the reagents to the embedding material, tissue matrix did not result in significant background, unlike other reagents that are fluorescent and require extensive washing.

To induce hydroxyl radicals, sections are incubated with a mixture of 100 µM $FeSO_4$ and 100 µM $H_2O_2$ for 0, 10, 30 and 60 minutes and then the analysis repeated to detect enhanced reaction with pro-fluorophore hydrazines and the commercial alternatives ARP, FARP, anti-8-OxodG antibody and the OxyDNA kit. Positive results with the pro-fluorophore hydrazines are then evaluated to assess their use without additional washing steps as a direct stain for oxidative damage. Finally, sections from tumors excised under conditions that may have induced elevated levels of ROS are examined and stained to determine if this will be reflected in higher staining of pro-fluorophore hydrazine probes or the commercial alternatives.

Example 4

Tissue Culture and Differentiation of HL60 Cells

An ideal in vitro model for circulating blood neutrophils is unavailable insofar as neutrophils are terminally differentiated and a culturable untransformed granulocyte precursor cell line is not available. The human promyelocytic leukemia cell line HL60 is a granulocyte progenitor that can be induced to differentiate into functional neutrophils by treatment with all-trans retinoic acid ("ATRA") (Breitman et al. Chem. Res. Toxicol. 9:115, 1980). HL60 cells are used as a neutrophil cell model to develop and optimize our DNA damage detection and quantitation methods.

Figure 11D:
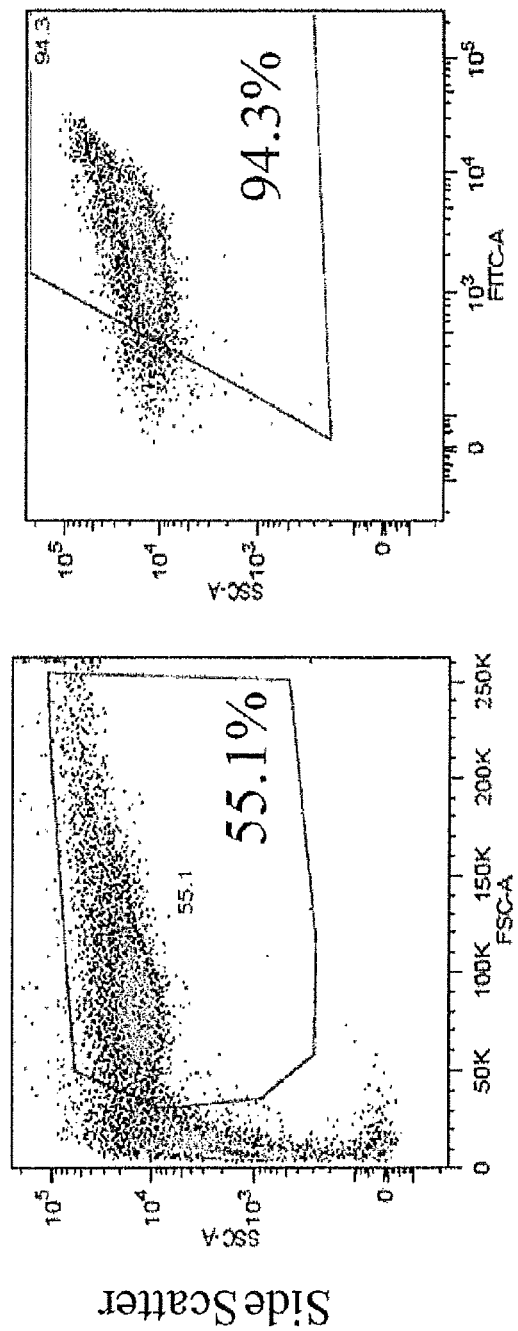
FIG. 11: In vitro differentiation of the HL60 promyelocytic leukemia cell line to neutrophils with all transretinoic acid, Vitamin D3 and GMCSF. Flow cytometry for forward scatter and CD 11b. (A) no treatment, (B) 1% ethanol, (C) 1 µM ATRA and (D) 1 µM ATRA, 6 pM. Vitamin D3 and 30 ng/mL G-CSF.

We have obtained the HL60 cell line and demonstrated in vitro differentiation to neutrophils. HL60 cells were grown to confluence ($1 \times 10^6$ cells/ml) in Roswell Park Memorial Institute media ("RPMI") 1640 media supplemented with 10% fetal bovine serum, 1% penicillin/streptomycin and 2 mM L-glutamine at 37° C. in 5% $CO_2$ and treated with ethanol carrier, 1 µM ATRA or 1 µM ATRA, 6 nM Vitamin $D_3$ and 30 ng/ml G-CSF for five days. Differentiation was confirmed by expression of the neutrophil-specific membrane receptor CD11b. Dot plot display of flow cytometry analysis using FITC-labeled mouse anti-human CD11b, a granulocyte marker, demonstrates increased expression of CD11b (mean fluorescien isothiocyanate, "FITC") correlated with increased granularity (mean SSC) in the differentiated cells (FIG. 11). Note that the data shown are gated to remove a significant fraction of apparently apoptotic cells in the differentiated cell populations. Gross morphological changes suggestive of neutrophil differentiation are apparent in the differentiated HL60 cells as revealed by Wright's-Giemsa stain, including an increase in the cytoplasm to nucleus ratio, a reduction in cell size and the characteristic increased lobularity of the nucleus (not shown).

Example 5

Pro-fluorescent Detection of 5-FodU in Cellular DNA 1. 5-FodU labeled DNA Chromosomal DNA is labeled with 5-FodU by several methods, including chemical oxidation, irradiation and incorporation in living cells. Salmon sperm DNA is dissolved in water at >10 mg/ml. Chemical oxidants such as peroxide or iron based Fenton reagents readily oxidize the 5-methyl group of thymine in solution or in DNA to an aromatic aldehyde, forming 5-FodU. Methods developed by Kasai et al. 1990, supra who treated duplex DNA with Fe(II)-EDTA, Fe(II)-nitriloacetic acid (NTA), Fe(III)-EDTA-$H_2O_2$-catecholo or ascorbic acid-$H_2O_2$ are utilized. Interestingly, Kasai (Mutat. Res., 243:249, 1990) found that 5-FodU was generated more efficiently than 8-OxodG by this treatment. In this experiment, 10 mg aliquots of the DNA are diluted in solution to 0.5 mg/ml, treated with 100 μM $FeSO_4$ and 100 μM $H_2O_2$ at 37° C. Time points for analysis of base oxidation are recorded. For irradiation, 10 mg aliquots are diluted to 0.5 mg/ml and subjected to irradiation in a $^{60}Co$ source (~1.5 Gy/min) at doses of 0 to 100 Gy.

2. DNA labeled with 5-FodU by metabolic incorporation The methods of Klungland et al. (Toxicol. Lett., 119:71, 2001) who fed 5-FodU to tissue culture cells is utilized. They observed significant toxicity, with an $IC_{50}$ of ~1 μM in several cell lines. Toxicity was lost in cells lacking thymidine kinase or thymidylate synthetase and 5-FodU was found to be highly mutagenic, each suggesting incorporation into DNA. In this experiment, 5-FodU was added to tissue culture media for cancer cell lines, including HL60 promyelocytic leukemia cells, K562 myeloid leukemia cells and one or more adherent cell lines such as HeLa and MCF-7 and maximum tolerated doses were determined, where cell growth rate, as judged by time to confluence, is increased by less than two fold and cell death, as judged by ethidium bromide exclusion, is less than doubled. Cells are split and then placed into media at this 5-FodU concentration and allowed to reach confluence, and then DNA is prepared from these cells using Qiagen DNAEasy Blood & Tissue genomic DNA purification kits (Hilden, Germany). The concentration of the DNA is determined by $OD_{260nm}$. The DNA is stored at −80° C. to reduce the rate of depurination, adduct formation or other events.

Figure 12:
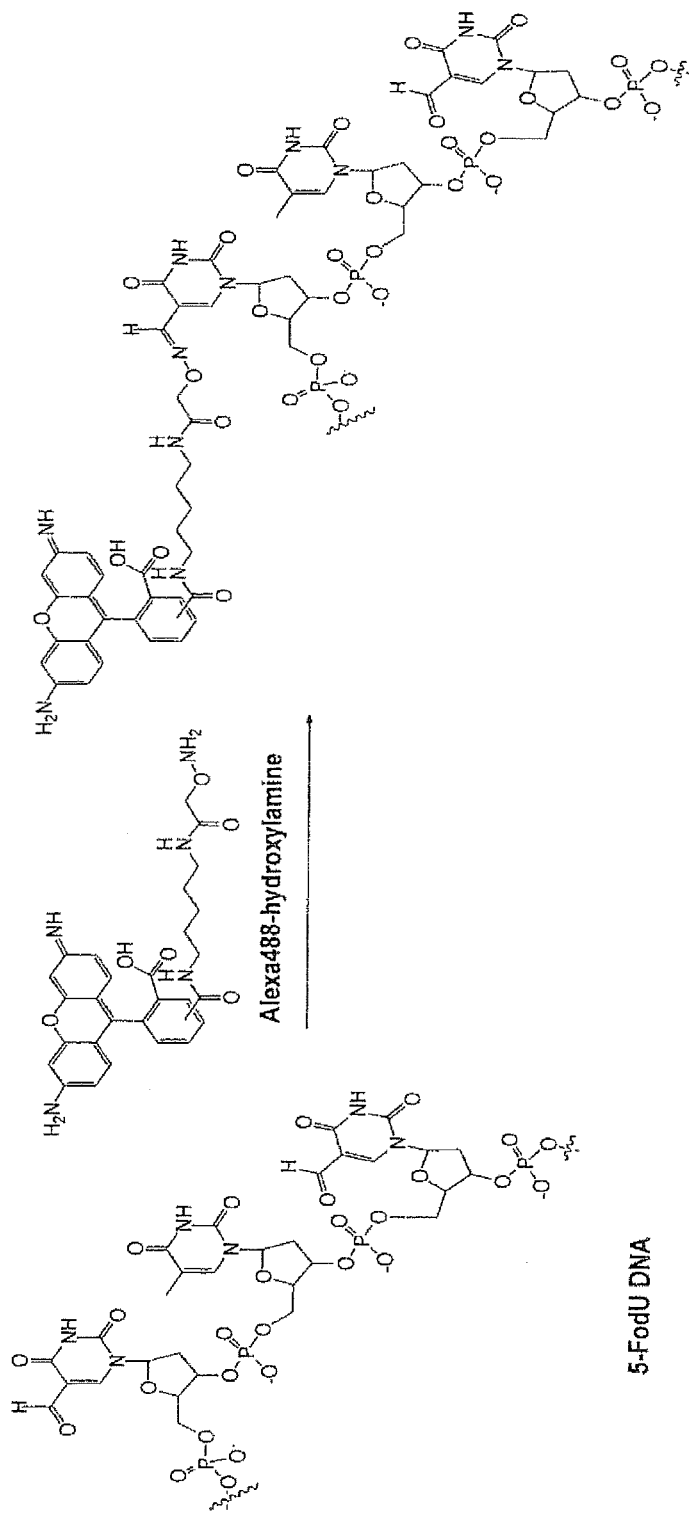
FIG. 12: Scheme for the reaction of FARP probe, Alexa Fluor® 488 hydroxylamine and 5-FodU DNA.

3. Quantitation of 5-FodU by conventional methods To detect formation of 5-FodU in chromosomal DNA, established methods for detection by GC-MS or HPLC-MS/MS (e.g. Hong and Wang Anal. Chem., 79:322, 2007, Douki et al. Chem. Res. Toxicol. 9:1145, 1996 and Cadet et al. Free Radic. Biol. Med. 33:441, 2002) are utilized. Chemically synthesized 5-FodU will be utilized to optimize methods and provide calibration standards. The labeled DNA is reacted with ARP and/or FARP probes (FIG. 12), to examine sensitivity of detection. In this experiment, DNA is treated with restriction enzymes or sonication and separated by TBE agarose gel electrophoresis to determine the extent of labeling of intact DNA. To determine ARP binding, DNA is transferred to nylon membranes and probed with fluorescent avidin. For FARP, the gel is imaged in a fluorescence flat bed scanner. Specificity of detection by ARP and FARP is examined by adding competing aldehydes such as simple aliphatic aldehydes, protein carbonyls and lipid aldehydes to the labeled DNA. ARP and FARP results are compared to the GC-MS and/or HPLC-MS/MS data to determine relative sensitivity, specificity and linearity of these methods.

4. Reaction of aromatic hydrazines with 5-FodU-labeled DNA. Using the optimal conditions defined above for labeling 5-FodU in solution, labeled DNA is treated with aromatic hydrazines including 2-hydrazinoquinoline, 3-methyl-2-benzothiazolinone hydrazone, 6-hydrazinonicotinamide, 4-hydrazinostilbazole and xantheny-9-ylidene hydrazine. The fluorescence enhancement, Stokes shift and reaction kinetics are quantified. Labeled DNA is digested with restriction enzymes or sonicated and separated on agarose gels to demonstrate that fluorescence is associated with the intact DNA. Specificity of detection by aromatic hydrazines is examined by adding competing aldehydes such as simple aliphatic aldehydes, protein carbonyls and lipid aldehydes to the labeled DNA. Results are then compared with the GC-MS and/or HPLC-MS/MS data and the ARP/FARP probe results.

Example 6

Demonstrate Pro-Fluorescent Detection of 5-FodU in Cells by Flow Cytometry

1. Fluorescence detection of incorporated 5-FodU in intact cells Detection of 5-FodU in cells is performed using known methods for analysis of DNA content by propidium iodide staining and detection of 8-Oxo-dG by anti-8-Oxo-dG antibody and manufacturer's protocols for the OxyDNA and OxyFLOW kits. Briefly, aliquots of ~$10^6$ cells, starting with K562 or HL60 suspension cells, are obtained by growth to confluence in the presence of a range of tolerated concentrations of 5-FodU and lightly fixed with paraformaldehyde and permeabilized with saponin, Triton X-100 or other surfactant (e.g. Becton Dickenson CytoFix/Cytoperm reagent Franklin Lakes, N.J.), washed in PBS and then treated with RNAse and trypsin. DNA content was determined by staining cells with Hoechst 33242, propidium iodide, SYTOX Blue, Green or Orange or other DNA stain and evaluated by flow cytometry using the University of Chicago Flow Cytometry Facility FACSCanto or FACSCalibur analyzers (Chicago, Ill.). Controls were screened for background reactivity for the pro-fluorophore hydrazines including 2-hydrazinoquinoline, 3-methyl-2-benzothiazolinone hydrazone, Xanthen-ylidene hydrazine, and 4-hydrazinostilbazole, with and without 100 mM aniline, and compared to commercially available reagents including ARP and FARP (Invitrogen, San Diego, Calif.), anti-8-OxodG antibody and the OxyDNA and/or OxyFLOW kits. The reagents were added, incubated and washed with PBS and screened by fluorescence imaging, flow cytometry and/or 96 well plate fluorimetry. A small positive signal should result in all cells but any hydrazine probes that display high fluorescent enhancement will be rejected. The reactivity of aromatic hydrazine probes is examined to detect incorporated 5-FodU using the optimal conditions developed above. In this experiment, the reagents were added, incubated, washed and conventional fluorimetry, quantitative imaging, and/or flow cytometry were used to examine the background signal in the absence of 5-FodU and determine the fluorescence enhancement with increasing 5-FodU incorporation.

One or more aromatic hydrazines will display higher signal to background and more rapid kinetics and greater consistency when evaluated as a ratio between a total DNA stain and the 5-FodU reactivity, when evaluated by flow cytometry. When performing dual staining, the DNA stain will have to be at a relatively low stoichiometry to avoid cross-talk and probe-probe interactions, such as fluorescence energy transfer and quenching. In particular, the sensitive and specificity for 5-FodU is evaluated using the advanced flow cytometers at the University of Chicago. A point-of-care flow cytometer based assay was evaluated on an Accuri benchtop flow cytometer (Accuri Cytometers, Ann Arbor, Mich.) equipped with standard laser and filters. The optics is adapted to optimize detection and enhance signal to noise ratio.

2. Analysis of 5-FodU formation by hydroxyl radicals and ionizing radiation in tissue culture cells Non-adherent HL60 and K562 myeloid cell lines, are washed, permeabilized and fixed with paraformaldehyde, and then washed in PBS. Free radical damage is induced in the fixed tissue culture cells, by treatment with a mixture of 100 µM $FeSO_4$ and 100 µM $H_2O_2$ for 0, 10, 30 and 60 minutes. The analysis is then repeated to detect enhanced reaction with pro-fluorophore hydrazines and the commercial alternatives ARP, FARP, anti-8-OxodG antibody and the OxyDNA and/or OxyFLOW kits. The suspension culture cells are stained with a DNA counterstain (e.g. Syber Green) and examined by microscopy to determine whether the fluorescent product demonstrates localization, primarily or exclusively to the nucleus. ARP, FARP, anti-8-OxodG antibody, and OxyDNA/FLOW led to moderate background in control cells and all showed enhanced binding, with highest intensity in the nucleus after treatment with hydroxyl radicals. For the aromatic hydrazines, their reactivity will be specific to aromatic aldehydes. Thus fluorescence is low, but nuclear localized in the controls and restricted to nucleic acids in oxidized cells. Cytoplasmic staining can also be detected due to oxidized RNA. To test if cytoplasmic background is indeed due to RNA, the cells are treated with RNAse prior to staining. Flow cytometry is then performed, plus and minus RNAse, using a DNA counterstain such as Syber Green to provide a ratio of staining to DNA content, and evaluate homogeneity of staining and compare the intensity distributions of populations of control and oxidized cells, to compare the hydrazines and commercial reagents.

Living cells are irradiated in the $^{60}Co$ irradiator (~1.5 Gy/min) at doses of 0 to 50 Gy. Aliquots of ~$10^6$ cells are removed from each sample for DNA extraction and conventional analysis of oxidative damage by GC/MS. 5-FodU content and kinetics of removal from DNA are determined. For staining, cells are fixed with paraformaldehyde. An aliquot is stained with FARP, anti-8-OxodG antibody and the OxyDNA and/or OxyFLOW kits using manufacturer's protocols, and analyzed by quantitative imaging and flow cytometry. The aromatic hydrazine probes to detect 5-FodU are examined each, with and without aniline, to accelerate kinetics. In this investigation, the reagents are added, the cells incubated, washed and analyzed by fluorimetry, quantitative imaging, and/or flow cytometry to develop plots of fluorescence enhancement vs. incubation time. Data is obtained to determine sensitivity and linearity and to compare performance to FARP, anti-8-OxodG and the OxyDNA/OxyFLOW kits. FARP, anti-8-OxodG antibody, and OxyDNA/FLOW led to moderate background in control cells and showed enhanced binding, with highest intensity in the nucleus after irradiation. Aromatic hydrazine pro-fluorescence detection was substantially better than commercial reagents.

5-FodU formation by ionizing radiation is detected by established methods for detection, GC-MS or HPLC-MS/MS (e.g. Hong and Wang Anal. Chem., 2007 supra, Douki et al., 1996, supra and Cadet et al., 2002, supra). Using the optimal conditions defined above, the irradiated DNA is treated with aromatic hydrazines including 2-hydrazinoquinoline, 3-methyl-2-benzothiazolinone hydrazone, 6-hydrazinonicotinamide, and 4-hydrazinostilbazole. The fluorescence enhancement, Stokes shift and reaction kinetics is quantified and the results correlated with the ARP probe and the GC-MS results. Suspension culture cells are stained with a DNA counterstain (e.g. Syber Green) and examined by microscopy to determine whether the fluorescent product demonstrates localization, primarily or exclusively to the nucleus. Some cytoplasmic staining may be due to oxidized RNA. Consequently, the cells are treated with RNAse prior to staining. Under these conditions staining of cells using hydrazines is substantially better than commercial reagents.

3. HL60 cell differentiation and purification Neutrophils are both a readily accessible cell type for biodosimetry and a significant target tissue in ARS. Consequently, HL60 cells are a neutrophil model for biodosimetry. While this promyelocytic leukemia cell line may not be an optimal model, the ability to reproducibly grow large numbers of cells, and differentiate them into functional neutrophils makes this a powerful system. Because of unexpected results that might occur when differentiating HL60 cells while simultaneously labeling them metabolically with 5-FodU only differentiated, HL60 cells were used in this investigation to validate pro-fluorophore detection of 5-FodU in irradiated cells.

Human promyelocytic leukemia HL60 cells are cultured in RPMI 1640 media supplemented with 10% FBS, 1% Pen/Strep and 2 mM GT at 37° C. with 5% $CO_2$ at a culture density maintained at $10^5$ to $10^6$ cells/ml. Confluent cultures at $1\times10^6$ cells/ml are subjected to a standard protocol to induce differentiation into functional neutrophils by incubation with 1 µM ATRA, 6 µM 1,25-dihydroxy Vitamin D3 and 30 ng/ml GCSF (Bunce et al. Leukemia 9:410, 1995). Differentiation is evaluated and the assay optimized balancing extent of differentiation against loss of cells to apoptosis. Density gradient centrifugation is used to isolate the differentiated neutrophils from apoptotic cells, cell debris and any undifferentiated cells. Several methods have been described using Percoll, Ficoll, Hypaque and/or Nycodenz gradients (e.g. Ford et al. Blut 54:337, 1987, McFaul J. Immunol. Methods 130:15, 1990, Kalmer et al. J. Immunol. Methods 110:275, 1988, Kjeldsen et al. J. Immunol. Methods 232:131, 1999, Lichtenberger et al. J. Immunol. Methods 227:75, 1999 and Kouoh et al. Biol. Pham. Bull. 23:1382, 2000) to isolate functional, unactivated neutrophils. Typically, the purity of these preparations is 95-98%. Cells are washed free of the gradient material and resuspended in cold neutrophil buffer (e.g. 20 mM HEPES, 132 mM NaCl, 6 mM KCl, 1 mM $MgSO_4$, 1 mM $KH_2PO_4$, 5 mM glucose, 1.0 mM $CaCl_2$, 0.05% BSA, pH 7.4) before irradiation and analysis.

4. Neutrophils from anticoagulated human blood Anticoagulated venous blood obtained from patients at the University of Chicago Adult Primary Care service and to be discarded after hematocrit and differential are obtained as needed. High yields of unactivated neutrophils are obtained by one of several validated protocols for purification of neutrophils using gradient centrifugation as described above. The one-step gradient method can be optimized to obtain a >50% yield with >95% purity. Neutrophils are then examined for viability and function prior to analysis.

5. Flow cytometric detection of 5-FodU in neutrophils after irradiation Aliquots of both differentiated HL60 and human neutrophils are fixed with paraformaldehyde, permeabilized, washed in PBS and then screened for background reactivity for the pro-fluorophore hydrazines including 2-hydrazinoquinoline, 3-methyl-2-benzothiazolinone hydrazone, 6-hydrazinonicotinamide, and 4-hydrazinostilbazole. In this experiment, the reagents are added, incubated, then washed with PBS and screened by fluorescence imaging and flow cytometry. A small positive signal in all cells is observed, but probes that display high fluorescent enhancement are rejected. Then, >10⁶ each of differentiated HL60 cells, or human neutrophils, are subjected to $^{60}$Co irradiation at doses from 0 to 10 Gy. Aliquots of each sample are subjected to DNA extraction and the content of 5-FodU determined by conventional analysis of oxidative damage by GC/MS. Similarly, aliquots are removed and fixed with paraformaldehyde. An aliquot is stained to detect 8-OxodG with anti-8-OxodG antibody and the OxyDNA and/or OxyFLOW kits using the manufacturer's protocols, and analyzed by quantitative imaging and flow cytometry. The pro-fluorophore probes are then examined to detect 5-FodU, using standard conditions developed above. In this experiment, the reagents are added and fluorimetry, quantitative imaging, and/or flow cytometry are used to develop plots of fluorescence enhancement vs. radiation dose, to determine sensitivity and linearity and to compare performance. Conditions are optimized for flow cytometric detection as well as the requirement for proteolysis, RNAse treatment, and/or other extractions to enhance detection and quantitation, for adapting the assay to the Accuri benchtop flow cytometer.

6. Detection of 5-FodU in living tissue culture cells and neutrophils Living K562 and undifferentiated HL60 cells are labeled with 5-FodU by metabolic incorporation using aromatic hydrazines in the media or buffer, with and without aniline. The cells are screening to determine those hydrazines judged to be most promising as candidates for use in living cells. More specifically, the cells are screened for low background and high fluorescence enhancement at the excitation and emission maxima for the predicted hydrazone product using fluorimetry and fluorescence imaging. Changes in cell integrity and viability are examined during staining. 5-FodU formation in K562 and undifferentiated HL60 cells as well as differentiated HL60 and human neutrophils subjected to $^{60}$Co irradiation at doses from 0 to 50 Gy is detected. The living cells are then assayed on the Accuri benchtop flow cytometer to detect 5-FodU and the optics further optimized to enhance detection of formation of the expected hydrazones.

These experiments demonstrate that measuring and detecting oxidative damage in tissues can be accomplished using aromatic hydrazine probes to detect the aromatic aldehydes 5-FodU and 5-FodC via covalent reaction to form a fluorescent bis-arylhydrazone product by flow cytometry.

Example 7

Homogenous Surface-Based Assay for 5-FodU in Solution and in DNA

Figure 9A:
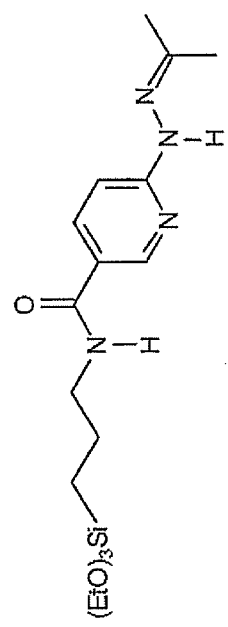
FIG. 9: (A) HyNic silane and (B) HyNic-silanized glass surface.
Figure 9B:
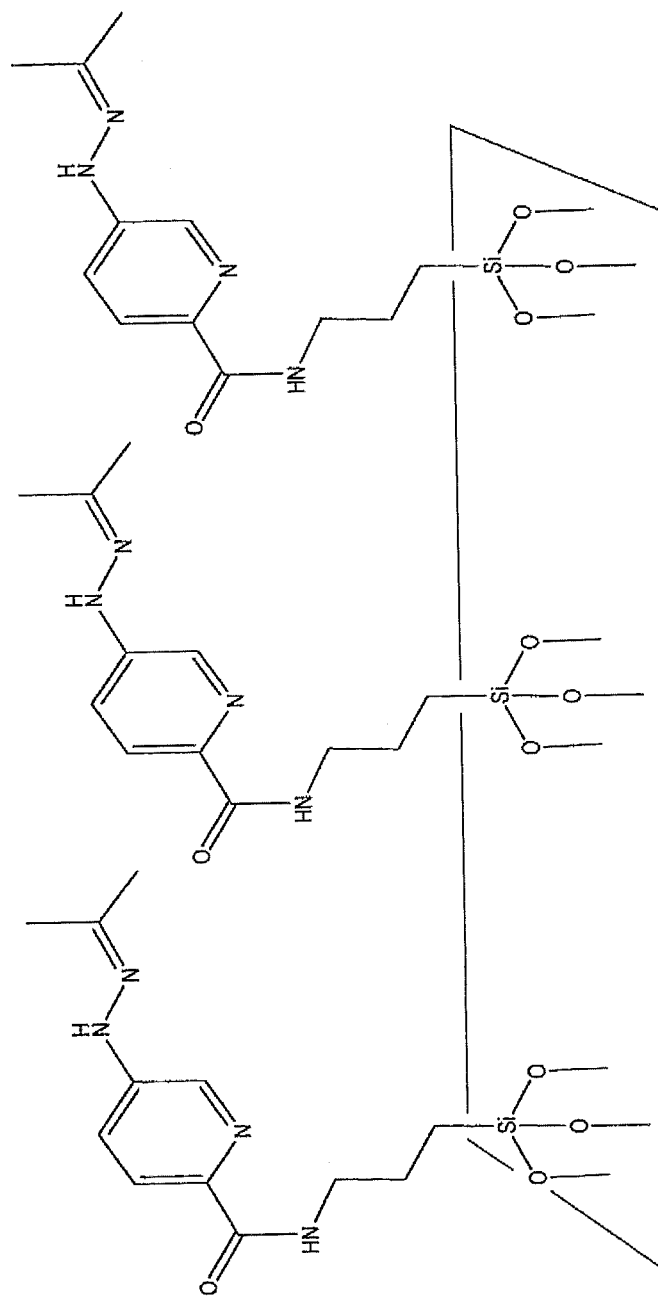

A condition of the successful development of a lateral flow test is the capture of the analyte in a zone on a test strip as the analyte flows through. Silica surfaces such as glass slides, coverslips, glass wool, controlled pore glass and/or silica beads are modified with HyNic-silane (FIG. 9). HyNic-modified glass surfaces are exposed to synthetic 5-FodU in aqueous solution, with and without 10-100 mM aniline. Fluorimetry or fluorescent imaging is used to detect the formation of a fluorescent product on the surface. FIG. 10, presents fluorescence properties of the hydrazone formed from the reaction of 4-formylbenzamide and 6-hydrazinonicotinamide. The bis-arylhydrazone formed from HyNic and 5-FodU has similar fluorescent characteristics and is detected using the 365 nm mercury line and standard "DAPI" fluorescence filters and optics in an epifluorescence microscope.

The surface based assay format is used to detect 5-FodU formed from irradiation of chromosomal DNA. Samples subjected to the full range of radiation doses and assay intact DNA, denatured DNA and DNA hydrolyzed with DNAse I are used. 5-FodU-based hydrazones are detected by fluorimetry and/or fluorescence imaging.

Example 8

Homogeneous Solution Phase and Surface Assays for 5-FodU in Cell Lysates

Whole cell lysates of neutrophil-differentiated HL60 cells are prepared to capture the nucleotide pools, RNA and DNA, all of which may contain 5-FodU after irradiation. To prepare cell lysates, the cells are suspended in RIPA (1% Triton X100, 0.1% SDS, 1% deoxycholate) or another detergent lysis buffer. The cells are then disrupted with a needle and syringe, incubated at 4° C. for 30 minutes and sonicated. Protease, DNAse and/or RNAse is added to fully solubilize the nucleic acids. Lysates from unirradiated cells and cells treated with doses from 0 to 10 Gy are prepared as stated above. Fluorimetry is utilized to examine the reactivity for pro-fluorophore hydrazines including 2-hydrazinoquinoline, 3-methyl-2-benzothiazolinone hydrazone, 6-hydrazinonicotinamide, and 4-hydrazinostilbazole, with and without 10-100 mM aniline. Background fluorescence is evaluated to examine sensitivity by adding synthetic 5-FodU and determining the limits of detection, linearity and kinetics. Cell lysates may contain a competitor or inhibitor that could increase fluorescent background, so that the solution phase homogeneous assay can be optimized to enhance the observed signal above background.

Surface-based assay might be optimal with a whole cell lysate. To implement the surface based assay, cell lysates are applied to HyNic silane coated glass (as slides, coverslips, or beads) and the accumulation of fluorescent product on the glass surface over time is observed. Background, sensitivity for added synthetic 5-FodU and detection of irradiation is observed as described above. The effect of conditions such as aniline or buffers on kinetics is examined. The need to wash away the lysate prior to measuring fluorescence is determined for the assay.

The examples set forth above are provided to give those of ordinary skill in the art with a complete disclosure and description of how to make and use the preferred embodiments of the compositions, and are not intended to limit the scope of what the inventor regards as their invention. Modifications of the above-described modes (for carrying out the invention that are obvious to persons of skill in the art) are intended to be within the scope of the following claims. All publications, patents and patent applications cited in this specification are incorporated herein by reference.

We claim:

1. A method for detecting DNA damage in a subject suspected of having DNA damage characterized by the formation of aryl aldehyde moieties in DNA, comprising the steps of:
   a) combining a sample comprising DNA from the subject with a pro-fluorescent aromatic hydrazine compound selected from the group consisting of 2-hydrazinoquinoline, 3-methyl-2-benzothiazolinone, 6-hydrazinonicotinamide and 4-hydrazinostilbazole to label the DNA with a bis-aryl hydrazone formed between the pro-fluorescent aromatic hydrazine compound and an 5-FodU aryl aldehyde moiety formed as a result of damage to the DNA, the bis-aryl hydrazone within the DNA having a fluorescent emission distinct from the fluorescent emission of the aryl aldehyde and the aryl hydrazine;
   b) detecting the fluorescent DNA by monitoring the fluorescent emission of the bis-aryl hydrazone; and
   c) quantitating the fluorescent emission to determine the DNA damage.

2. The method according to claim 1, wherein the DNA damage in the subject is the result of the subject being exposed to ionizing radiation or oxidizing chemicals.

3. The method according to claim 1, wherein the sample is an isolated DNA sample, a cell or a tissue sample.

4. The method of claim 1, wherein the pro-fluorescent hydrazine compound is 2-hydrazinoquinoline.

5. The method of claim 1, wherein the pro-fluorescent hydrazine compound is 3-methyl-2-benzothiazolinone.

6. The method of claim 1, wherein the pro-fluorescent hydrazine compound is 6-hydrazinonicotinamide.

7. The method of claim 1, wherein the pro-fluorescent hydrazine compound is 4-hydrazinostilbazole.

8. The method of claim 3, wherein the presence of fluorescent DNA is detected in a cell.

* * * * *

SEQUENCE LISTING

<160> NUMBER OF SEQ ID NOS: 9

<210> SEQ ID NO 1
<211> LENGTH: 24

```
<212> TYPE: DNA
<213> ORGANISM: Artificial Sequence
<220> FEATURE:
<223> OTHER INFORMATION: Synthetic

<400> SEQUENCE: 1
gtacctgatg tagcagacag tctc                                              24

<210> SEQ ID NO 2
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is 5-formyldeoxyuridine

<400> SEQUENCE: 2
gnacctgatg tagcagacag tctc                                              24

<210> SEQ ID NO 3
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: n is 5-formyldeoxyuridine

<400> SEQUENCE: 3
gtacctgatg nagcagacag tctc                                              24

<210> SEQ ID NO 4
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is 5-formyldeoxyuridine
<220> FEATURE:
<221> NAME/KEY: misc_feature
<222> LOCATION: (11)..(11)
<223> OTHER INFORMATION: n is 5-formyldeoxyuridine

<400> SEQUENCE: 4
gtaccngatg nagcagacag tctc                                              24

<210> SEQ ID NO 5
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: n is 5-formyldeoxyruidine
<220> FEATURE:
<221> NAME/KEY: misc_feature
<222> LOCATION: (21)..(21)
<223> OTHER INFORMATION: n is 5-formyldeoxyruidine

<400> SEQUENCE: 5
gtacctgatg nagcagacag nctc                                              24
```

<210> SEQ ID NO 6
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is 5-formyldeoxyuridine
<220> FEATURE:
<221> NAME/KEY: misc_feature
<222> LOCATION: (23)..(23)
<223> OTHER INFORMATION: n is 5-formyldeoxyuridine

<400> SEQUENCE: 6
gnacctgatg tagcagacag tcnc                                              24

<210> SEQ ID NO 7
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is 5-formyldeoxyuridine
<220> FEATURE:
<221> NAME/KEY: misc_feature
<222> LOCATION: (11)..(11)
<223> OTHER INFORMATION: n is 5-formyldeoxyuridine
<220> FEATURE:
<221> NAME/KEY: misc_feature
<222> LOCATION: (23)..(23)
<223> OTHER INFORMATION: n is 5-formyldeoxyuridine

<400> SEQUENCE: 7
gnacctgatg nagcagacag tcnc                                              24

<210> SEQ ID NO 8
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is 5-formyldeoxyuridine
<220> FEATURE:
<221> NAME/KEY: misc_feature
<222> LOCATION: (9)..(9)
<223> OTHER INFORMATION: n is 5-formyldeoxyuridine
<220> FEATURE:
<221> NAME/KEY: misc_feature
<222> LOCATION: (11)..(11)
<223> OTHER INFORMATION: n is 5-formyldeoxyuridine

<400> SEQUENCE: 8
graccngang nagcagacag tctc                                              24

<210> SEQ ID NO 9
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is deoxyuridine

```
<220> FEATURE:
<221> NAME/KEY: misc_feature
<222> LOCATION: (9)..(9)
<223> OTHER INFORMATION: n is deoxyuridine
<220> FEATURE:
<221> NAME/KEY: misc_feature
<222> LOCATION: (11)..(11)
<223> OTHER INFORMATION: n is deoxyuridine

<400> SEQUENCE: 9
gtaccngang nagcagacag tctc                                              24
```